(12) United States Patent
Murphy et al.

(10) Patent No.: US 11,291,458 B2
(45) Date of Patent: *Apr. 5, 2022

(54) VASO-OCCLUSIVE DEVICE AND DELIVERY ASSEMBLY

(71) Applicants: STRYKER CORPORATION, Kalamazoo, MI (US); STRYKER EUROPEAN OPERATIONS HOLDINGS LLC, Kalamazoo, MI (US)

(72) Inventors: Richard Murphy, Sunnyvale, CA (US); Hancun Chen, San Ramon, CA (US)

(73) Assignees: STRYKER CORPORATION, Kalamazoo, MI (US); STRYKER EUROPEAN OPERATIONS HOLDINGS LLC, Kalamazoo, MI (US)

(*) Notice: Subject to any disclaimer, the term of this patent is extended or adjusted under 35 U.S.C. 154(b) by 443 days.

This patent is subject to a terminal disclaimer.

(21) Appl. No.: 16/402,089

(22) Filed: May 2, 2019

(65) Prior Publication Data
US 2019/0254676 A1 Aug. 22, 2019

Related U.S. Application Data

(63) Continuation of application No. 15/542,924, filed as application No. PCT/US2016/066521 on Dec. 14, 2016, now Pat. No. 10,321,915.
(Continued)

(51) Int. Cl.
*A61B 17/12* (2006.01)

(52) U.S. Cl.
CPC ...... *A61B 17/1215* (2013.01); *A61B 17/1214* (2013.01); *A61B 17/12113* (2013.01); *A61B 2017/12054* (2013.01)

(58) Field of Classification Search
CPC ............ A61B 17/1215; A61B 17/1214; A61B 17/12113; A61B 2017/12054;
(Continued)

(56) References Cited

U.S. PATENT DOCUMENTS

| 4,994,069 A | 2/1991 | Ritchart et al. |
| 8,202,292 B2 | 6/2012 | Kellett |

(Continued)

FOREIGN PATENT DOCUMENTS

| EP | 0618783 A1 | 10/1994 |
| EP | 0618783 B1 | 7/2003 |

(Continued)

OTHER PUBLICATIONS

International Search Report and Written Opinion of the International Searching Authority dated May 11, 2017 for PCT/US2016/066521, with International filing date of Dec. 14, 2016, Applicant Stryker Corporation, (19 pages).

(Continued)

*Primary Examiner* — Amy R Weisberg
(74) *Attorney, Agent, or Firm* — Vista IP Law Group, LLP

(57) ABSTRACT

A vaso-occlusive treatment system includes a delivery assembly; and a vaso-occlusive device detachably coupled to the delivery assembly by a delivery assembly junction. The vaso-occlusive device includes a braided portion formed out of one or more composite wires, a coiled portion coupled to the braided portion, and an intra-device junction coupling the braided portion to the coiled portion. Each composite wire includes a core made from a core metallic material, and an external layer made from an external metallic material different from the core metallic material. One of the core and the external layer has a greater radiopac-
(Continued)

ity and a lesser stiffness, respectively, than the other one of the core and the external layer.

10 Claims, 31 Drawing Sheets

Related U.S. Application Data

(60) Provisional application No. 62/341,789, filed on May 26, 2016, provisional application No. 62/269,867, filed on Dec. 18, 2015.

(58) Field of Classification Search
CPC ...... A61B 17/12163; A61B 2017/1205; A61B 2017/12063
See application file for complete search history.

(56) References Cited

U.S. PATENT DOCUMENTS

| | | | |
|---|---|---|---|
| 9,480,479 | B2 | 11/2016 | Chen et al. |
| 10,321,915 | B2 * | 6/2019 | Murphy ............ A61B 17/1215 |
| 2002/0143361 | A1 | 10/2002 | Douk |
| 2002/0151927 | A1 | 10/2002 | Douk |
| 2004/0220608 | A1 | 11/2004 | D'Aquanni |
| 2006/0135986 | A1 | 6/2006 | Wallace et al. |
| 2006/0155324 | A1 | 7/2006 | Porter |
| 2006/0184194 | A1 | 8/2006 | Pal |
| 2007/0049964 | A1 | 3/2007 | Dunfee |
| 2007/0149996 | A1 | 6/2007 | Coughlin |
| 2007/0239194 | A1 | 10/2007 | Tran et al. |
| 2008/0103522 | A1 | 5/2008 | Steingisser |
| 2011/0054519 | A1 | 3/2011 | Neuss |
| 2013/0116722 | A1 | 5/2013 | Aboytes |
| 2013/0253572 | A1 | 9/2013 | Molaei et al. |
| 2014/0260238 | A1 | 9/2014 | Marion, III et al. |
| 2014/0277091 | A1 | 9/2014 | Breedlove |
| 2015/0057700 | A1 | 2/2015 | Chen |
| 2015/0313605 | A1 | 11/2015 | Griffin |
| 2016/0066918 | A1 | 3/2016 | Chen |
| 2016/0249934 | A1 | 9/2016 | Hewitt |
| 2017/0035437 | A1 | 2/2017 | Sarge |
| 2017/0354402 | A1 | 12/2017 | Lee |

FOREIGN PATENT DOCUMENTS

| | | |
|---|---|---|
| JP | 2013-027592 A | 2/2013 |
| WO | WO 2004008974 A1 | 1/2004 |
| WO | WO 2008036156 A1 | 3/2008 |
| WO | WO 2014 0105932 A1 | 7/2014 |
| WO | WO 2017106265 A1 | 6/2017 |

OTHER PUBLICATIONS

Extended European Search Report for EP Patent Appln. No. 18182747.8, dated Oct. 15, 2018 (8 pages).
Corrected version of the European Search Opinion for EP Patent Appln. No. 18182747.8, dated Nov. 14, 2018 (4 pages).
Foreign Office Action for JP Patent Appln. No. 2018-530724 dated Sep. 25, 2020.

* cited by examiner

Distal joint, Pre_tensile_Design4

33% 15ms Laser Weld around Marker
16 ends braid od 0.0008"Nitinol_24 picks/inch
*Metallic Marker 0.0085"ID, 0.0105"OD, 0.025" length*

VASO-OCCLUSIVE DEVICE AND DELIVERY ASSEMBLY

RELATED APPLICATIONS DATA

The present application is a continuation of U.S. patent application Ser. No. 15/542,924 filed Jul. 11 2017, which is a National Phase entry under 35 U.S.C § 371 of International Patent Application No. PCT/US2016/066521, having an international filing date of Dec. 14, 2016, and which claims the benefit under 35 U.S.C. § 119 to U.S. Provisional Application Ser. No. 62/269,867, filed Dec. 18, 2015, and 62/341,789, filed May 26, 2016. The foregoing applications are hereby incorporated by reference into the present application in their entirety.

FIELD

The field of the disclosed inventions generally relates to vaso-occlusive devices for establishing an embolus or vascular occlusion in a vessel of a human patient. More particularly, the disclosed inventions relate to at least partially braided or woven vaso-occlusive devices, junctions within such devices and junctions for coupling such devices to delivery systems.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" assembly or "wire" is then passed through the micro-catheter, until a vaso-occlusive device coupled to a distal end of the delivery assembly is extended out of the distal end opening of the micro-catheter and into the aneurysm. Once in the aneurysm, portions of the vaso-occlusive device deform or bend to allow more efficient and complete packing. The vaso-occlusive device is then released or "detached" from the distal end of the delivery assembly, and the delivery assembly is withdrawn back through the catheter. Depending on the particular needs of the patient, one or more additional vaso-occlusive devices may be pushed through the catheter and released at the same site.

One well-known way to release a vaso-occlusive device from the end of the delivery assembly is through the use of an electrolytically severable junction, which is a small exposed section or detachment zone located along a distal end portion of the delivery assembly. The detachment zone is typically made of stainless steel and is located just proximal of the vaso-occlusive device. An electrolytically severable junction is susceptible to electrolysis and disintegrates when the delivery assembly is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher completes an electrolytic detachment circuit with a return electrode, and the detachment zone disintegrates due to electrolysis. Other detachment mechanisms for releasing a vaso-occlusive device from a delivery assembly include mechanical, thermal, and hydraulic mechanisms.

In order to better frame and fill aneurysms, complex three-dimensional secondary shapes can be imparted on vaso-occlusive coils and the stiffness/flexibility of vaso-occlusive coils can be modified. However, vaso-occlusive coils continue to have performance limitations including breaking performance, shape retention and anchoring ability.

The proximal end of some vaso-occlusive devices is coupled to the distal end of the delivery assembly with an adhesive at what is known as a "major junction" of the vaso-occlusive treatment system, or a "delivery assembly junction." Another major junction design is disclosed in U.S. Pat. No. 8,202,292, issued to Kellett, which is fully incorporated herein by reference as though set forth in full. The major junction includes a flat adapter coupling a delivery wire to a vaso-occlusive coil. The delivery wire has a hook or "J" shape distal end configured to be received in an aperture in the proximal end of the adapter to couple the delivery wire to adapter. The vaso-occlusive coil has windings that define openings configured to receive fingers in the distal end of the adapter to couple the vaso-occlusive coil to the adapter. Consequently, the adapter facilitates coupling of the delivery wire to the vaso-occlusive coil. Other major junction designs are disclosed in U.S. patent application Ser. No. 14/457,970, by Chen et al., which is fully incorporated herein by reference as though set forth in full.

While major junctions coupled with an adhesive and those including a flat adapter have performed well, coupling of the delivery assembly and the vaso-occlusive device can be improved. Accordingly, there remains a need for other systems and methods for coupling a vaso-occlusive device to a delivery assembly at a major junction.

SUMMARY

In one embodiment, an implantable vaso-occlusive device includes a braid formed out of one or more drawn filled tubes. Each drawn filled tube includes a core made from a core metallic material, and an external layer made from an external metallic material different from the core metallic material. Each of the core and external metallic materials has a respective radiopacity and a respective stiffness. One of the core and external metallic materials has a greater radiopacity and a lesser stiffness, respectively, than the other one of the core and external metallic materials. Each of the one or more drawn filled tubes has a "yield strength to ultimate strength" ratio of less than 80%.

In one or more embodiments, the core metallic material comprises platinum, and the external metallic material comprises Nitinol. In other embodiments, the core metallic material comprises Nitinol, and the external metallic material comprises platinum. The braid may include first and second drawn filled tubes that are twisted together. Each of the one or more drawn filled tubes may have a "yield strength to ultimate strength" ratio of less than 70%, 60% or 50%.

In another embodiment, an implantable vaso-occlusive device includes a braid formed out of 16-48 drawn filled tubes. Each drawn filled tube has a core comprising platinum and an external layer comprising Nitinol. Each of the plurality of drawn filled tubes has a platinum content of 35% to 60% by volume, and an outer diameter of 0.0010 in. to 0.0015 in.

In one or more embodiments, the braid is formed out of 24-32 drawn filled tubes, each having a platinum content of 40% to 50% by volume, and an outer diameter of 0.00115 in. to 0.00125 in. The Nitinol may have an austenite finish temperature between 30° C. and 45° C. The drawn filled tubes may include an oxide coating.

In another embodiment, a vaso-occlusive treatment system includes a delivery assembly and a vaso-occlusive device detachably coupled to the delivery assembly by a delivery assembly junction, wherein the vaso-occlusive device includes a braided portion, a coiled portion, and an intra-device junction coupling the braided portion to the coiled portion.

In one or more embodiments, the braided portion includes a proximal end and a middle, where a diameter of the proximal end is less than a diameter of the middle. The braided portion may include a distal end and a middle, where a diameter of the distal end is less than a diameter of the middle. The coiled portion may include a proximal end and a middle, where a diameter of the proximal end is less than a diameter of the middle. The coiled portion may include a distal end and a middle, where a diameter of the distal end is less than a diameter of the middle.

In one or more embodiments, the delivery assembly has a distal end, where the distal end forms a hook. The braided portion may include an elongate member forming a loop at a proximal end thereof. The hook may pass through the loop, thereby coupling the delivery assembly and the vaso-occlusive device. The vaso-occlusive device may have a reduced diameter proximal end configured to prevent the hook from moving proximally.

In various embodiments, the delivery assembly junction includes a link having a proximal end and a distal end, and the distal end of the link includes a plurality of fingers. The plurality of fingers may be configured to interface between adjacent elongate members of the braided portion. The plurality of fingers may be configured to interface between adjacent opening windings of the coiled portion.

In one or more embodiments, the delivery assembly junction includes a braided member, and at least a portion of the braided member is disposed radially inside of the vaso-occlusive device.

In one or more embodiments, the delivery assembly junction includes a tubular body disposed around least a portion of the vaso-occlusive device. The tubular body may include a metallic band and/or a laminated polymer tube.

In one or more embodiments, the vaso-occlusive device includes a stretch-resisting member. The stretch-resisting member may be an elongate member and/or a braided tube. The intra-device junction may include a loop formed at a proximal end of the stretch-resisting member. The loop may encircle an elongate member of the braided portion to anchor the stretch-resisting member thereto. The loop may encircle a reduced diameter portion of the vaso-occlusive device to anchor the stretch-resisting member thereto. The intra-device junction may include a wire having a hook formed at an end thereof, and the hook may pass through the loop.

In one or more embodiments, the intra-device junction includes an enlarged body formed at a proximal end of the stretch-resisting member, and the enlarged body is disposed adjacent a reduced diameter portion of the vaso-occlusive device to anchor the stretch-resisting member thereto. The intra-device junction may include a hook formed at a proximal end of the stretch-resisting member. A central portion of the stretch-resisting member may be configured to facilitate articulation of the vaso-occlusive device. The stretch-resisting member may include an elongate member, which also forms at least a part of the vaso-occlusive device.

In one or more embodiments, the intra-device junction includes a tubular body disposed around least a portion of the vaso-occlusive device. The tubular body may be a metallic band and/or a laminated polymer tube.

In one or more embodiments, the intra-device junction includes a tubular body disposed in a lumen defined by a portion of the vaso-occlusive device. The tubular body may include a braided tube, a coil and/or a solid body. The intra-device junction may include a pin extending radially through the braided and coiled portions, thereby coupling the braided and coiled portions. The coiled portion may include a flattened winding disposed at an end thereof. A long axis of the flattened winding may be substantially parallel to a longitudinal axis of the vaso-occlusive device.

In one or more embodiments, the braided portion includes a braided distal end, and the coiled portion includes a coiled proximal end. The braided distal end may be disposed inside of the coiled proximal end. The coiled proximal end may be disposed inside of the braided distal end.

In one or more embodiments, the braided portion includes a braided proximal end, and the coiled portion includes a coiled distal end. The braided proximal end may be disposed inside of the coiled distal end. The coiled distal end may be disposed inside of the braided proximal end. The coiled portion may be configured to facilitate articulation of the vaso-occlusive device.

In accordance with another aspect, embodiments of the disclosed inventions include vaso-occlusive treatment systems having a delivery assembly and a vaso-occlusive device detachably coupled to the delivery assembly by a severable junction, the vaso-occlusive device including a proximal coil having an inner axial lumen and a proximal end portion coupled to the severable junction, and a braid having a proximal end portion coupled to a distal end portion of the proximal coil by a first intra-device junction, the braid comprising a plurality of elongate braid members, wherein two or more of the braid members extend proximally from the braid through the axial lumen of proximal coil and are secured to the proximal end portion of the proximal coil, respectively, to thereby form proximal coil stretch-resisting members.

In one such embodiment, each of the proximal coil stretch-resisting members has a proximal end attached to a distal portion of the severable junction that is coupled to the proximal end portion of the proximal coil, the severable junction being configured such that the distal portion of the severable junction remains coupled to the proximal end portion of the proximal coil when the severable junction is severed. By way of one, non-limiting example, the proximal ends of the proximal coil stretch-resisting members may comprise respective hooks that engage an aperture formed in the distal portion of the severable junction. Similarly, the vaso-occlusive member may include a distal coil having a proximal end portion attached to a distal end portion of the braid by a second intra-device junction, the distal coil having an inner axial lumen, wherein the same or a different two or more of the braid members extend distally from the braid through the axial lumen of distal coil and are secured to the distal end portion of the distal coil, respectively, to thereby form distal coil stretch-resisting members. In such embodiments, the vaso-occlusive device may further comprise a distal end joint coupled to the distal end portion of the distal coil and formed at least in part by joining together respective distal ends of the distal coil stretch-resisting members.

In accordance with still another embodiment of the disclosed inventions vaso-occlusive treatment systems have a delivery assembly and a vaso-occlusive device detachably coupled to the delivery assembly by a severable junction, the vaso-occlusive device including a distal coil having an inner axial lumen and a braid having a distal end portion coupled to a proximal end portion of the proximal coil by an intra-device junction, the braid comprising a plurality of elongate braid members, wherein two or more of the braid members extend distally from the braid through the axial lumen of distal coil and are secured to a distal end portion of the distal proximal coil, respectively, to thereby form distal coil stretch-resisting members.

In one such embodiment, the system also includes a distal end joint coupled to the distal end portion of the distal coil and formed at least in part by joining together respective distal ends of the distal coil stretch-resisting members.

In accordance with yet another aspect of the disclosed inventions, an implantable vaso-occlusive device includes a braid formed out of one or more elongate braid members, each elongate braid member comprising a core, an intermediate layer at least partially surrounding the core, and an outer layer at least partially surrounding the intermediate layer, each of the core, intermediate layer and outer lays being composed of metallic materials, and each having a respective radiopacity and a respective stiffness, wherein one of the core, intermediate layer and outer layer has a greater radiopacity and/or a lesser stiffness than the other ones. By way of one, non-limiting example, the core metallic materials may comprise platinum, the intermediate layer metallic materials may comprise Nitinol, and the outer layer metallic materials may comprise titanium. By way of another, non-limiting example, the core may comprise a radiopaque metallic materials, the intermediate layer may comprise a superelastic metallic material, and the outer layer may comprise an oxidation resistant metallic material. By way of yet another, non-limiting example, the core may have a higher radiopacity than the each of the intermediate layer and outer layer, the intermediate layer may have a lower stiffness than each of the core and the outer layer, and the outer layer may have a higher resistance to oxidation than each of the core and the intermediate layer.

In still another embodiment, a vaso-occlusive treatment system includes a delivery assembly; and a vaso-occlusive device detachably coupled to the delivery assembly by a delivery assembly junction. The vaso-occlusive device includes a braided portion formed out of one or more composite wires, a coiled portion coupled to the braided portion, and an intra-device junction coupling the braided portion to the coiled portion. Each composite wire includes a core made from a core metallic material, and an external layer made from an external metallic material different from the core metallic material. One of the core and the external layer has a greater radiopacity and a lesser stiffness, respectively, than the other one of the core and the external layer.

In one or more embodiments, the core metallic material includes platinum, and the external metallic material includes Nitinol. In other embodiments, the core metallic material includes Nitinol, and the external metallic material includes platinum.

In one or more embodiments, each of the one or more composite wires may have a yield strength to ultimate strength ratio of less than 80%.

In one or more embodiments, the braid portion includes a braid formed out of a plurality of composite wires, each composite wire having a core including platinum and an external layer including Nitinol, the plurality of composite wires consists of 16-48 composite wires, each of the plurality of composite wires has a platinum content of 35% to 60% by volume, and each of the plurality of composite wires has an outer diameter of 0.0010 in. to 0.0015 in.

In one or more embodiments, the plurality of composite wires consists of 24-32 composite wires, each having a platinum content of 40% to 50% by volume, and an outer diameter of 0.00115 in. to 0.00125 in.

In one or more embodiments, the delivery assembly has a distal end, where the distal end forms a hook. The delivery assembly junction may include a link having a proximal end and a distal end, where the distal end of the link includes a plurality of fingers. The delivery assembly junction may include a braided member, where at least a portion of the braided member is disposed radially inside of the vaso-occlusive device. The delivery assembly junction may include a tubular body disposed around least a portion of the vaso-occlusive device.

In one or more embodiments, the intra-device junction includes a tubular body disposed around least a portion of the vaso-occlusive device. The intra-device junction may include a tubular body disposed in a lumen defined by a portion of the vaso-occlusive device. The tubular body may include a braided tube.

In one or more embodiments, the intra-device junction includes a pin extending radially through the braided and coiled portions, thereby coupling the braided and coiled portions.

In one or more embodiments, the coiled portion includes a flattened winding disposed at an end thereof, a long axis of the flattened winding being substantially parallel to a longitudinal axis of the vaso-occlusive device.

In one or more embodiments, the braided portion has a substantially constant width.

In one or more embodiments, each of the core and external metallic materials have a respective radiopacity and a respective stiffness.

In one or more embodiments, each of the one or more composite wires has a yield strength to ultimate strength ratio of less than 80%.

In one or more embodiments, one of the core and the external layer provides radiopacity to the composite wire, while the other of the core and the external layer provides superelasticity and/or shape memory (i.e. the ability for the braid to recover to its original width) to the composite wire.

In one or more embodiments, the core is made from discontinuous segments of wire and/or powder. In such embodiments, the core would be less stiff than a comparable core made from a continuous wire.

In one or more embodiments, a width of the braided portion ranges from 0.5 mm to 2.5 mm. A width to thickness ratio of the braided portion may range from 1:1 to 40:1. A braid angle of the braided portion can range from 10° to 90°.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of various embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments of the disclosed inventions for purposes of illustration and facilitating the below detailed description, and are not therefore to be considered limiting of its scope.

DETAILED DESCRIPTION OF THE ILLUSTRATED EMBODIMENTS

Figure 1:
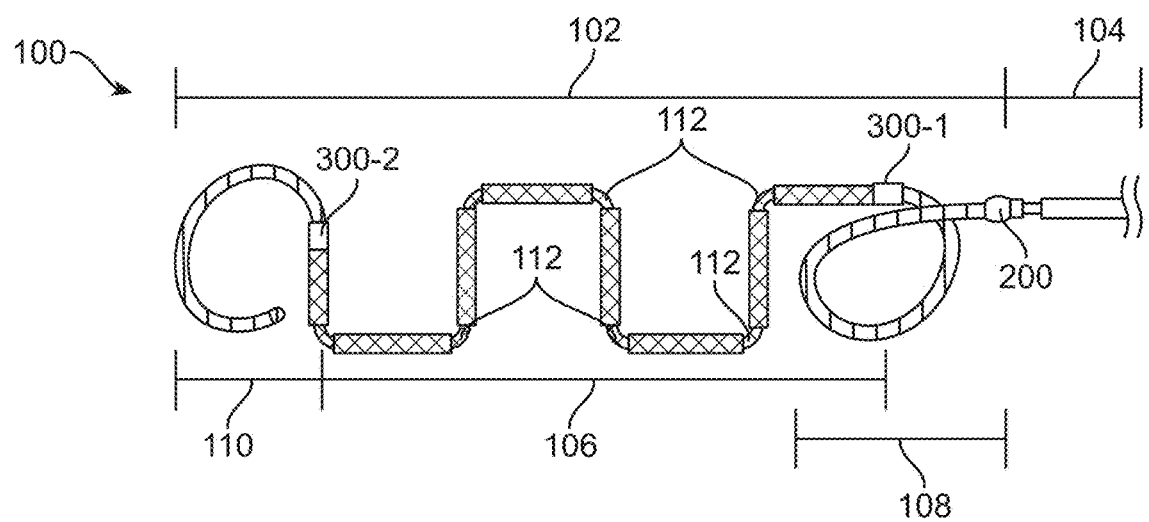
FIG. 1 is a schematic view of an exemplary vaso-occlusive treatment system, including a vaso-occlusive device and a delivery assembly constructed according to one embodiment.

This specification describes exemplary embodiments and applications of the disclosed invention. The disclosed invention, however, is not limited to these exemplary embodiments and applications or to the manner in which the exemplary embodiments and applications operate or are described herein. Further, the figures may show simplified or partial views, and the dimensions of elements in the figures may be exaggerated or otherwise not in proportion. Moreover, elements of similar structures or functions are represented by like reference numerals throughout the figures. In addition, an illustrated embodiment needs not have all the aspects or advantages shown. An aspect or an advantage described in conjunction with a particular embodiment is not necessarily limited to that embodiment, and can be practiced in any other embodiments even if not so illustrated.

For the following defined terms, these definitions shall be applied, unless a different definition is given in the claims or elsewhere in this specification.

As the terms "on," "attached to," "connected to," "coupled to," "secured to" or similar words are used herein, one element (e.g., a material, a layer, a substrate, etc.) can be "on," "attached to," "connected to," "coupled to" or "secured to" another element regardless of whether the one element is directly on, attached to, connected to, coupled to or secured to the other element or there are one or more intervening elements between the one element and the other element. Directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. The term "ones" means more than one.

All numeric values are herein assumed to be modified by the term "about," whether or not explicitly indicated. The term "about" generally refers to a range of numbers that one of skill in the art would consider equivalent to the recited value (i.e., having the same function or result). In many instances, he terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, a plurality of "elongate members" used to form a braid can include only a single elongate member used to form the braid, i.e., wherein the single elongate member turns back on itself at the ends of the braid. As used herein, the terms "tube," "tubular," "diameter," "radius" and "circumference" encompass objects with non-circular cross section as well as those with circular cross sections.

Figure 2:
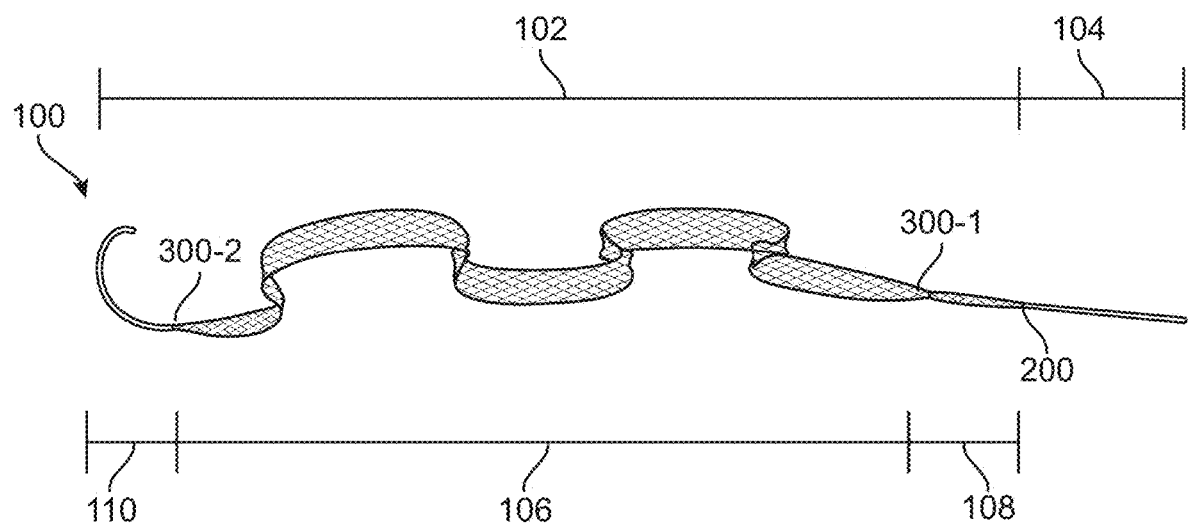
FIG. 2 is a photograph of the vaso-occlusive treatment system depicted in FIG. 1.

FIGS. 1 and 2 depict a vaso-occlusive treatment system 100 that includes an implantable vaso-occlusive device 102 coupled to a delivery assembly 104. The vaso-occlusive device 102 includes a central braided portion 106 disposed axially between proximal and distal portions 108, 110. A major junction 200 couples a distal end of the delivery assembly 104 to a proximal end of the proximal portion 108. The "major junction" is also known as a "delivery assembly junction." A proximal intra-device junction 300-1 couples the proximal end of the central portion 106 to a distal end of the proximal portion 108. A distal intra-device junction 300-2 couples the distal end of the central portion 106 to a proximal end of the distal portion 110.

The central portion 106 is a braided from drawn filled tubing ("DFT") elongate members (e.g., "wires"), such as those available from Fort Wayne Metals in Fort Wayne, Ind. DFTs are a type of composite wire. For instance, the central portion 106 can be braided from 24 DFT wires, each wire having a cross-sectional diameter of 0.00125 in. The braid can be a flat braid or a round braid. In other embodiments, the central portion 106 can be braided from 24 to 32 DFT wires, each wire having a cross-sectional diameter of 0.00115 in. to 0.00125 in. The proximal and distal portions 108, 110 are coils wound from one or more of the same DFT wires. In alternative embodiments, the proximal and distal portions 108, 110 may be coils wound from one or more substantially pure NiTi wire instead of DFT wires.

The DFT wire includes a substantially pure Platinum ("Pt") core at least partially surrounded by a substantially pure Nitinol ("NiTi") external layer. As used in this application, "substantially pure" Pt includes but is not limited to 99.95% commercial purity produced in accordance with ASTM B561. The Pt core is approximately 40%-50% of the DFT wire by volume ("Pt core content"). In some embodiments, the DFT wires are formed by inserting a core component (a solid elongate member) into an external component (a tubular elongate member) to form a composite elongate member (e.g., a composite wire). The composite elongate member is repeatedly mechanically drawn and annealed by heating to increase its axial length and decrease its cross-sectional diameter. For example, the drawing and annealing process can serially reduce the diameter of a composite elongate member from 1 in. to 0.5 in., from 0.5 in. to 0.25 in., from 0.25 in. to 0.025 in., and from 0.025 in. to 0.0025 in.

While the materials (e.g., Pt and NiTi) forming various portions (e.g., core and external layer) of the DFT wire may have different stiffnesses (i.e., bending stiffness), the relative stiffnesses (i.e., bending stiffness) of the resulting portions of the DFT may not necessarily reflect the stiffnesses of the material from which they are made. For instance, even though Pt's bending modulus (i.e., stiffness) is greater than that of NiTi, in various embodiments, Pt's bending modulus in combination with the Pt wire's diameter results in a platinum wire that is softer (i.e., less stiff) than the corresponding NiTi external layer.

Figure 5:
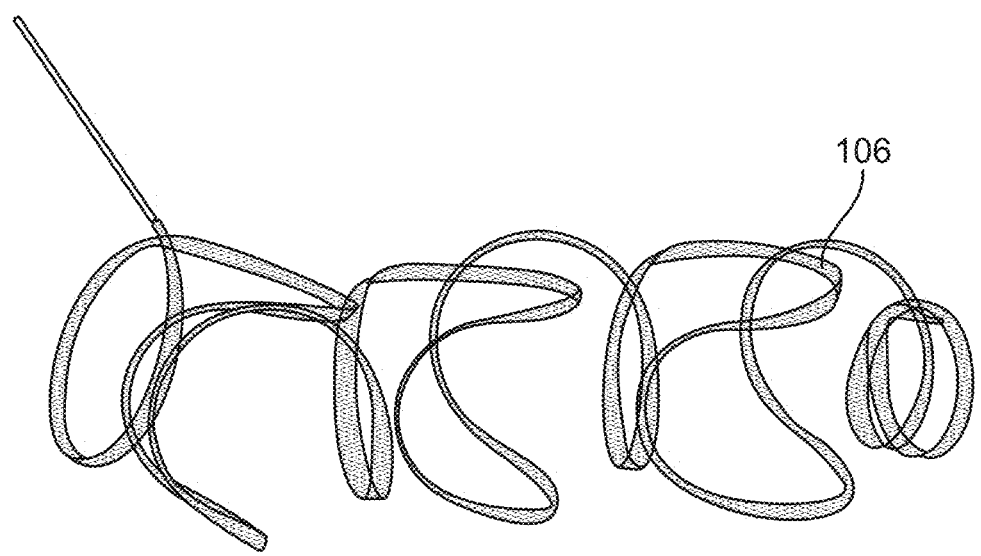
FIGS. 5 and 6 are photographs of unconstrained vaso-occlusive devices, constructed according to disclosed embodiments.
Figure 6:
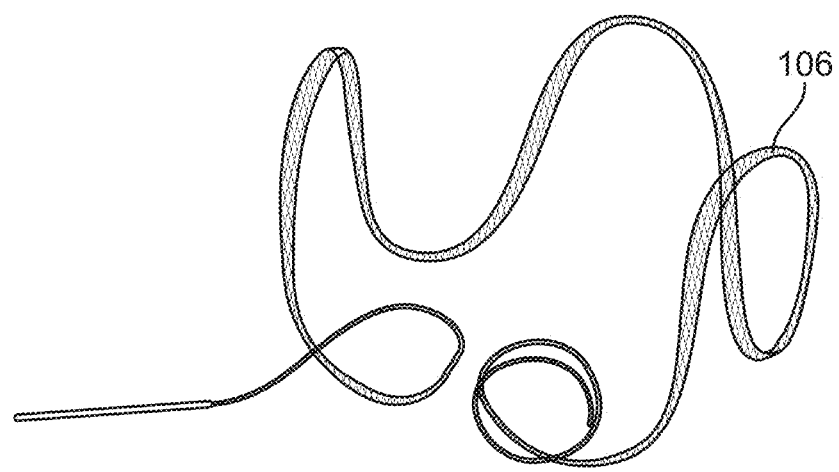

The central portion 106 of the vaso-occlusive device 102 can be braided on a mandrel, which can be flat or round depending on the desired final shape. After braiding, the central portion 106 can be heat set (e.g., at 500° C. to 550° C. for 1 to 10 minutes). The heat set completed braid forms the linear "primary shape" of the central portions 106. The heat set completed braid can then be wrapped around a second mandrel (e.g., a three-dimensional mandrel) and heat set for a second time to impart a three-dimensional "secondary shape." The NiTi external layer improves retention of the secondary shape, as shown in FIGS. 5 and 6.

While vascular implants (i.e., stents) have been formed from NiTi-DFT-Pt wires where the Pt core content is up to around 30%, NiTi-DFT-Pt wires with Pt core content around 40% to 50% have not been used to form stents. This is because stents typically require wires having higher yield strength to ultimate strength ratios (i.e., >80% of ultimate strength ("UTS")) to maintain vessel patency. On the other hand, the instant vaso-occlusive device 102 includes DFT wires with lower yield strength to UTS ratios, which improves device characteristics including lower bending moments and improved breaking performance. In various embodiments, the DFT wires that form (portions of) the vaso-occlusive device 102 have yield strength to UTS ratios of <50% UTS, <60% UTS, <70% UTS and <80% UTS. Yield strength is the maximum amount of force which can be applied to a material before it begins to plastically deform. UTS is the minimum amount of force which must be applied to a material before it fails. Braiding at least a portion of a vaso-occlusive device from wires having a yield strength to UTS ratio of less than 80% UTS is critical to simultaneously achieving the characteristics of improved radiopacity, shape retention and breaking performance.

Figure 3:
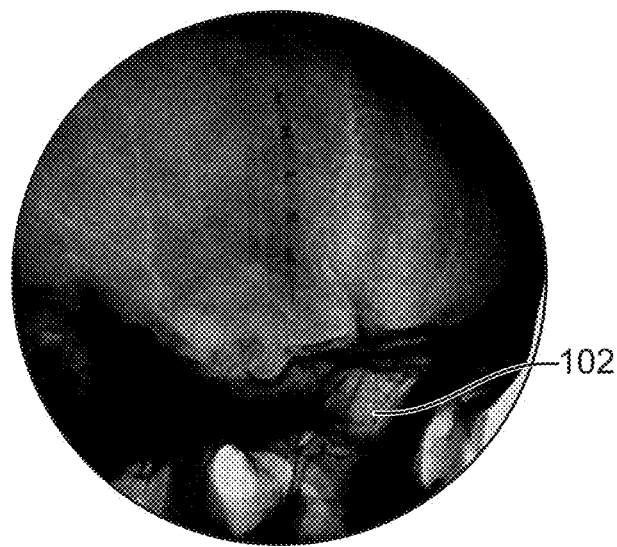
FIGS. 3 and 4 are images of the vaso-occlusive device depicted in FIG. 1 deployed in an animal vasculature.
Figure 4:
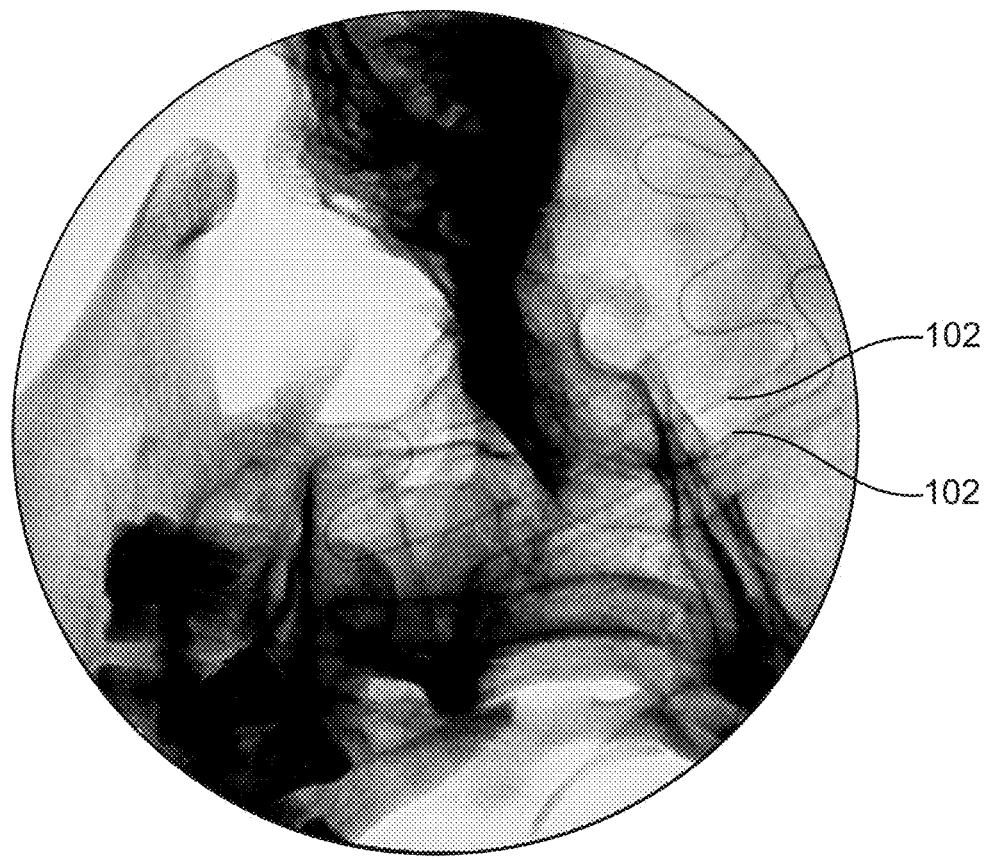

It was not previously known to form vascular implants, including vaso-occlusive devices, from NiTi-DFT-Pt wires with Pt core content of around 40% to 50%. Braiding the central portion 106 from DFT wires with Pt core content of around 40% to 50% ("NiTi-DFT-40/50Pt") provides a central portion 106 that has (1) radiopacity throughout its entire length, (2) improved shape retention, and (3) improved breaking performance along the entire length of the braid. The Pt core provides the radiopacity for a substantial proportion of the vaso-occlusive device 102, as shown in FIGS. 3 and 4. FIGS. 3 and 4 are radiographic images showing the radiopacity of various vaso-occlusive devices 102 implanted into patients. The radiographic image in FIG. 3 has the following characteristics: 1° caudal, 1° right anterior oblique, 69 kVp, and 1.36 mA. The radiographic image in FIG. 4 has the following characteristics: 1° caudal, 1° right anterior oblique, 100 kVp, and 3.73 mA. The superelastic properties of the NiTi external layer contribute to the improved shape retention. The softness of the Pt contributes to the improved breaking performance, i.e., the ability of the vaso-occlusive device 102 to bend and fold to conform to the shape of body cavities. These characteristics of the central portion 106 results in a vaso-occlusive device 102 that is more suitable for intra-saccular embolization of vascular defects, such as aneurysms, i.e., substantially consistent visualization grey scale throughout the device 102 and optimal softness profile.

Braiding at least a portion of a vaso-occlusive device 102 from 16 to 48 DFT wires, each wire having a cross-sectional diameter of 0.0010 in. to 0.0015 in. and having a Pt content of 35% to 60% is critical to simultaneously achieving the characteristics of improved radiopacity, shape retention and breaking performance. Unexpectedly, as the Pt content is increased, the effect of the increasing Pt content on decreasing flexible is reduced. Accordingly, braids woven from DFT wires having Pt content of 35% to 60% are surprisingly suitable for vaso-occlusive applications, e.g., endo-saccular applications requiring flexible devices. Such braids are especially well suited when they are woven from 16 to 48 DFT wires, each wire having a cross-sectional diameter of 0.0010 in. to 0.0015 in. In a preferred embodiment, at least a portion of a vaso-occlusive device 102 is braided from 24 to 32 DFT wires, each wire having a cross-sectional diameter of 0.00115 in. to 0.00125 in. and having a Pt content of 40% to 50%.

Normally the austenite finish, or "$A_f$" temperature of the NiTi is around 25° C., which is the temperature where the martensitic phase completes its transformation into the austenitic phase. Modifying the NiTi in the DFT such that its $A_f$ temperature is between 30° C. and 45° C. results in a softer vaso-occlusive device. Setting the $A_f$ temperature in this range achieves a desirable balance between device softness and conformability, which improves the suitability of the device for aneurysm treatment. Setting the $A_f$ of the NiTi can be accomplished by adjusting the composition of Ni in NiTi from the normal of 50% to 50.4%-50.8%. Further, the $A_f$ can be tuned with heat treatment of the NiTi. In a preferred embodiment, the $A_f$ temperature is between 38° C. and 40° C.

The DFT can also include an oxide coating with a controlled thickness, which will enhance thrombogenisis (e.g., clotting) to increase vaso-occlusion within aneurysms. Preferably, the oxide coating has an average thickness between 50 nm and 500 nm. This is contrary to previous DFT braided implants (e.g., stents), from which oxide coatings are substantially removed (e.g., via electro-polishing), to generate "bright" stents. In previous DFT braided stents, oxide coating thickness is limited to less than 50 nm.

Again referring to FIG. 1, the proximal and distal portions 108, 110 are atraumatic coils for minimize tissue damage during insertion and deployment of the vaso-occlusive device 102. The central portion 106 also includes predetermined breaking points 112, which are formed by twisting segments of the central portion 106 relative to each other or necking down points in the central portion 106 braid during formation of the secondary shape. In some embodiments, some breaking points 112 can include 90° bends for better anchoring with a body cavity. The delivery assembly 104 also includes an electrolytically degradable segment 114 at a distal end thereof. In other embodiments, alternative detachment mechanisms for releasing the vaso-occlusive device 102 from the delivery assembly 104 include mechanical, thermal, and hydraulic mechanisms.

Figure 7:
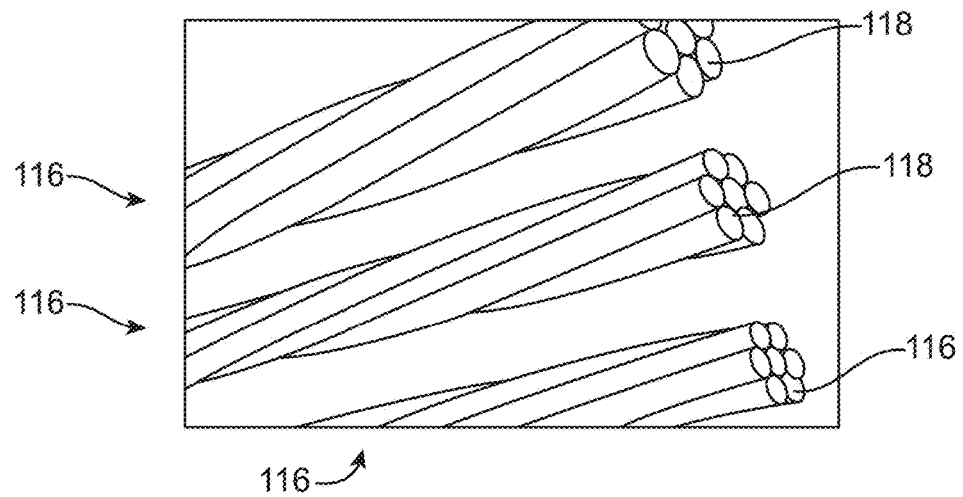
FIG. 7 is a perspective view of elongate members from which vaso-occlusive devices, or portions thereof, may be formed in accordance with the disclosed embodiments.

In other embodiments, instead of DFT wires, the central portion 106 may be braided from elongate members 116 formed from smaller DFT wires 118 twisted together, as shown in FIG. 7. Each DFT wire 118 may be made of Niti-DFT-40Pt. Braiding elongate members 116 (made from smaller DFT wires) instead of larger DFT wires results in a central portion 106 that is softer at approximately the same Pt core content. Accordingly, the central portion 106 according to this embodiment (i.e., twisted elongate member 116 braid) provides similar radiopacity with a softer braid. The braid according to this embodiment also provides higher surface area to promote thrombus formation, thereby enhancing aneurysm occlusion.

Figure 8:
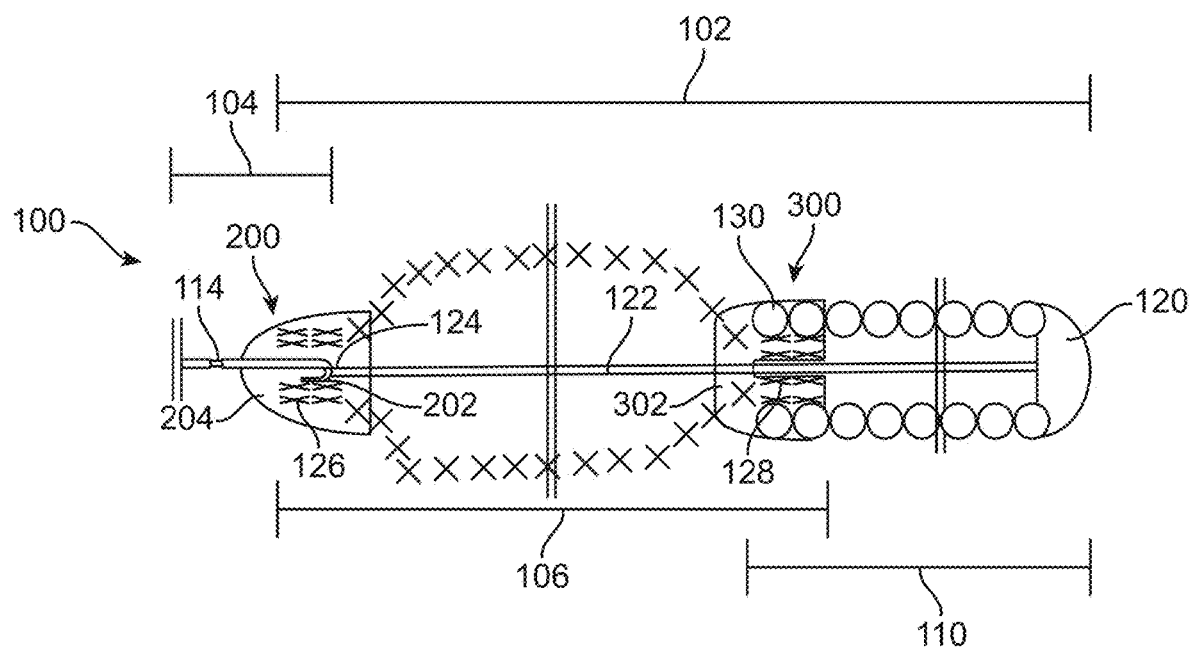
FIGS. 8-11 are longitudinal cross-section views of vaso-occlusive treatment systems, including vaso-occlusive devices constructed according to various disclosed embodiments.

FIG. 8 depicts a vaso-occlusive treatment system 100 according to one embodiment. The vaso-occlusive treatment system 100 includes a vaso-occlusive device 102 coupled to a delivery assembly 104 by a major junction 200. The delivery assembly 104 includes an electrolytically degradable segment 114 at a distal end thereof. The vaso-occlusive device 102 includes a central braided portion 106 coupled to a distal portion 110 by an intra-device junction 300. The central portion 106 is braided from DFT (i.e., composite) wires as described above, and has a substantially constant width (i.e., cross-sectional dimension). The distal coiled portion 110 is a coil wound from one or more DFT wires as described above. In other embodiments, the central and distal portions 106, 110 can be formed from other elongate members. The distal portion 110 also has an atraumatic distal tip 120, which may be formed from a small amount of adhesive. A stretch-resisting member 122 extends from the major junction 200, through the intra-device junction 300 and to the atraumatic distal tip 120, and reduces elongation of the vaso-occlusive device 102 as it is withdrawn proximally during delivery. The stretch-resisting member 122 can be made from a polymer (e.g., polypropylene) or a metal (e.g., NiTi).

The major junction 200 includes a hook 202 formed at the distal end of the delivery assembly 104. The hook 202 may be formed from a distal end of a core wire of the delivery assembly 104, as described in U.S. patent application Ser. No. 14/457,970, which was previously incorporated by reference. The stretch-resisting member 122 forms a proximal loop 124 at a proximal end thereof. The hook 202 passes through the proximal loop 124, mechanically coupling the delivery assembly 104 to the central portion 106 of the vaso-occlusive device 102. The major junction 200 also includes a necked down proximal end 126 of the central portion 106 of the vaso-occlusive device 102. The necked down proximal end 126 has a small profile that coupled to the hook 202. The proximal end 126 of the vaso-occlusive device 102 surrounds the hook 202 and the proximal loop 124 of the stretch-resisting member 122. The major junction 200 also includes an adhesive drop 204, which permeates the braided proximal end 126 of central portion 106 of the vaso-occlusive device 102 and binds together: (1) the hook 202 of the delivery assembly 104; (2) the proximal loop 124 of the stretch-resisting member 122; and (3) the proximal end 126 of the central portion 106 of the vaso-occlusive device 102, thereby forming the major junction 200.

The intra-device junction 300 includes a necked down distal end 128 of the central portion 106 of the vaso-occlusive device 102 and an open proximal end 130 of the distal portion 110 of the vaso-occlusive device 102. The distal end 128 of the central portion 106 is necked down so that it fits inside of the open proximal end 130 of the distal portion 110. The intra-device junction 300 also includes an adhesive drop 302, which permeates the coiled open proximal end 130 of the distal portion 110 of the vaso-occlusive device 102 and binds it together with the distal end 128 of the central portion 106 of the vaso-occlusive device 102 thereby forming the intra-device junction 300. Further, the adhesive drop 302 also binds the portion of the stretch-resisting member 122 passing through the intra-device junction 300.

Figure 9:
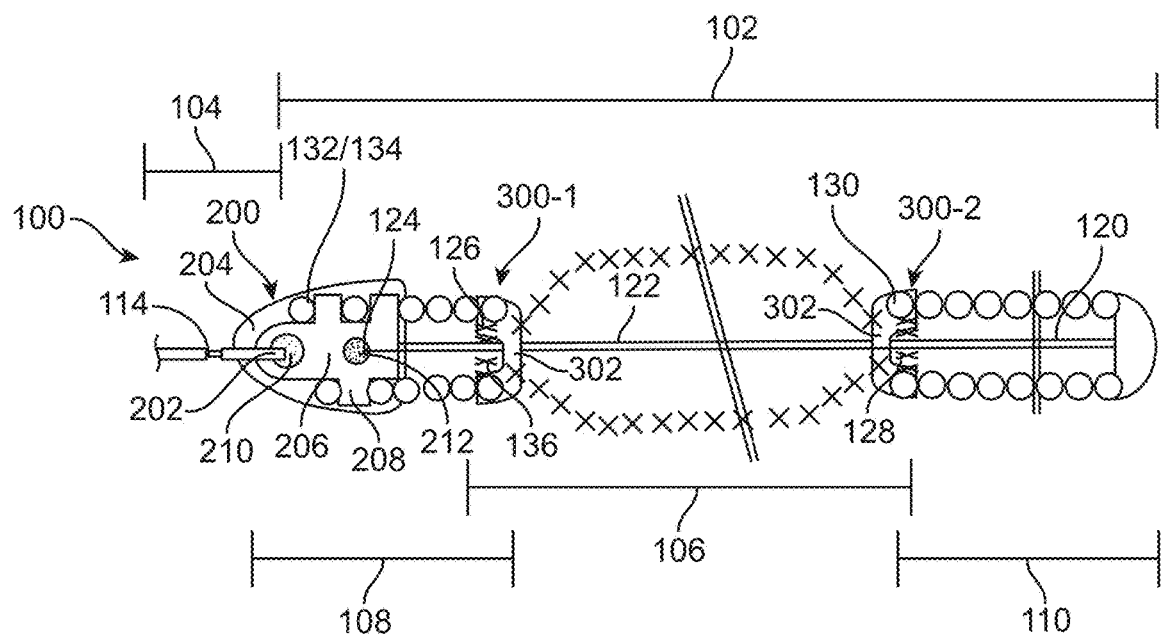

FIG. 9 depicts a vaso-occlusive treatment system 100 according to another embodiment. The vaso-occlusive treatment system 100 includes a vaso-occlusive device 102 coupled to a delivery assembly 104 by a major junction 200. The delivery assembly 104 includes an electrolytically degradable segment 114 at a distal end thereof. The vaso-occlusive device 102 includes a central braided portion 106 coupled to proximal and distal coiled portions 108, 110 by respective proximal and distal intra-device junctions 300-1, 300-2. The central portion 106 is braided from DFT (i.e., composite) wires as described above, and has a substantially constant width (i.e., cross-sectional dimension). The proximal and distal portions 108, 110 are coils wound from one or more DFT wires as described above. In other embodiments, the central, proximal and distal portions 106, 108, 110 can be formed from other elongate members. The distal portion 110 also has an atraumatic distal tip 120, which may be formed from a small amount of adhesive. A stretch-resisting member 122 extends from the major junction 200, through the intra-device junction 300 and to the atraumatic distal tip 120.

The major junction 200 includes a link/adapter 206 coupled to both the distal end of the delivery assembly 104 and the open proximal end 132 of the proximal portion 108, thereby coupling the delivery assembly 104 and the proximal portion 108. The link 206 may be formed from a sheet, as described in U.S. Pat. No. 8,202,292, which is incorporated herein by reference as though set forth in full. The link 206 is generally flat, and includes a plurality of fingers 208 formed in a proximal end thereof. The link 206 also includes proximal and distal apertures 210, 212. The proximal portion 108 of the vaso-occlusive device 102 is a coil with open pitch proximal windings 134 at the open proximal end 132 thereof. At least some of these proximal windings 134 interlace with the fingers 208 of the link 206, coupling the link 206 to the proximal portion 108 of the vaso-occlusive device 102.

The major junction 200 also includes a hook 202 formed from a distal end of a core wire of the delivery assembly 104, as described above. The hook 202 passes through the proximal aperture 210 of the link 206, coupling the delivery assembly 104 and link 206 (and the proximal portion 108 coupled thereto). The stretch-resisting member 122 forms a proximal loop 124 at a proximal end thereof. The proximal loop 124 passes through the distal aperture 212 of the link 206, mechanically coupling the link 206 (and the delivery assembly 104 coupled thereto) to the proximal portion 108 of the vaso-occlusive device 102. The major junction 200 also includes an adhesive drop 204, which permeates the open proximal end 132 of the vaso-occlusive device 102 through the open pitch proximal windings 134, and binds together: (1) the hook 202 of the delivery assembly 104; (2) the link 206; (3) the proximal loop 124 of the stretch-resisting member 122; and (4) proximal end 132 of the proximal portion 108 of the vaso-occlusive device 102, thereby forming the major junction 200.

The proximal and distal intra-device junctions 300-1, 300-2 are mirror images of each other. The proximal intra-device junction 300-1 includes an open distal end 136 of the proximal portion 108 of the vaso-occlusive device 102 and a necked down proximal end 126 of the central portion 106 of the vaso-occlusive device 102. The proximal end 126 of the central portion 106 is necked down so that it fits inside of the open distal end 136 of the proximal portion 108. The proximal intra-device junction 300-1 also includes an adhesive drop 302, which permeates the coiled open distal end 136 of proximal portion 108 of the vaso-occlusive device 102. The adhesive 302 binds together the proximal end 126 of the central portion 106 of the vaso-occlusive device 102 and the open distal end 136 of the proximal portion 108 of the vaso-occlusive device 102, thereby forming the proximal intra-device junction 300-1. Further, the adhesive drop 302 also binds the portion of the stretch-resisting member 122 passing through the proximal intra-device junction 300-1.

The distal intra-device junction 300-2 includes a necked down distal end 128 of the central portion 106 of the vaso-occlusive device 102 and an open proximal end 130 of the distal portion 110 of the vaso-occlusive device 102. The distal end 128 of the central portion 106 is necked down so that it fits inside of the open proximal end 130 of the distal portion 110. The distal intra-device junction 300-2 also includes an adhesive drop 302, which permeates the coiled open proximal end 130 of the distal portion 110 of the vaso-occlusive device 102. The adhesive 302 binds together the distal end 128 of the central portion 106 of the vaso-occlusive device 102 and the open proximal end 130 of the distal portion 110 of the vaso-occlusive device 102, thereby forming the distal intra-device junction 300-2. Further, the adhesive drop 302 also binds the portion of the stretch-resisting member 122 passing through the distal intra-device junction 300-2.

Figure 10:
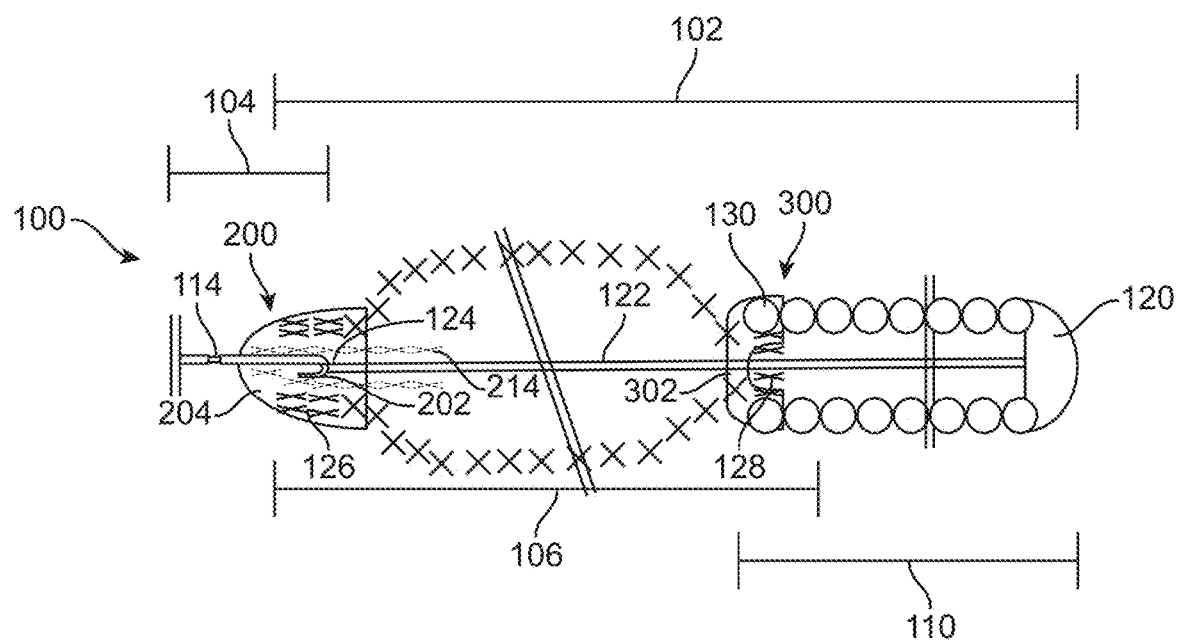

FIG. 10 depicts a vaso-occlusive treatment system 100 according to still another embodiment. The vaso-occlusive treatment system 100 depicted in FIG. 10 is almost identical to the vaso-occlusive treatment system 100 depicted in FIG. 8. One difference is that the major junction 200 also includes an inner braid 214 disposed radially between the hook 202 at the distal end of the delivery assembly 104 and the necked down proximal end 126 of the central portion 106 of the vaso-occlusive device 102. The inner braid 214 also surrounds the proximal loop 124 of the stretch-resisting member 122. The inner braid 214 can be woven from DFT, Pt and/or NiTi wires, as described above. The major junction 200 also includes an adhesive drop 204, which permeates the braided proximal end 126 of central portion 106 of the vaso-occlusive device 102 and binds together: (1) the hook 202 of the delivery assembly 104; (2) a proximal portion of the inner braid 214; (3) the proximal loop 124 of the stretch-resisting member 122; and (4) the proximal end 126 of the central portion 106 of the vaso-occlusive device 102, thereby forming the major junction 200. The inner braid 214 enhances pushability, reduces kinking of the central portion 106 (particularly at the major junction 200), and protects and strengthens the major junction 200. In particular, the inner braid 214 prevents kinking by bringing the respective effective stiffness of the distal end of the delivery assembly 104 and the proximal end of the vaso-occlusive device 102 closer together to minimize the stiffness differential, which can lead to kinking.

Figure 11:
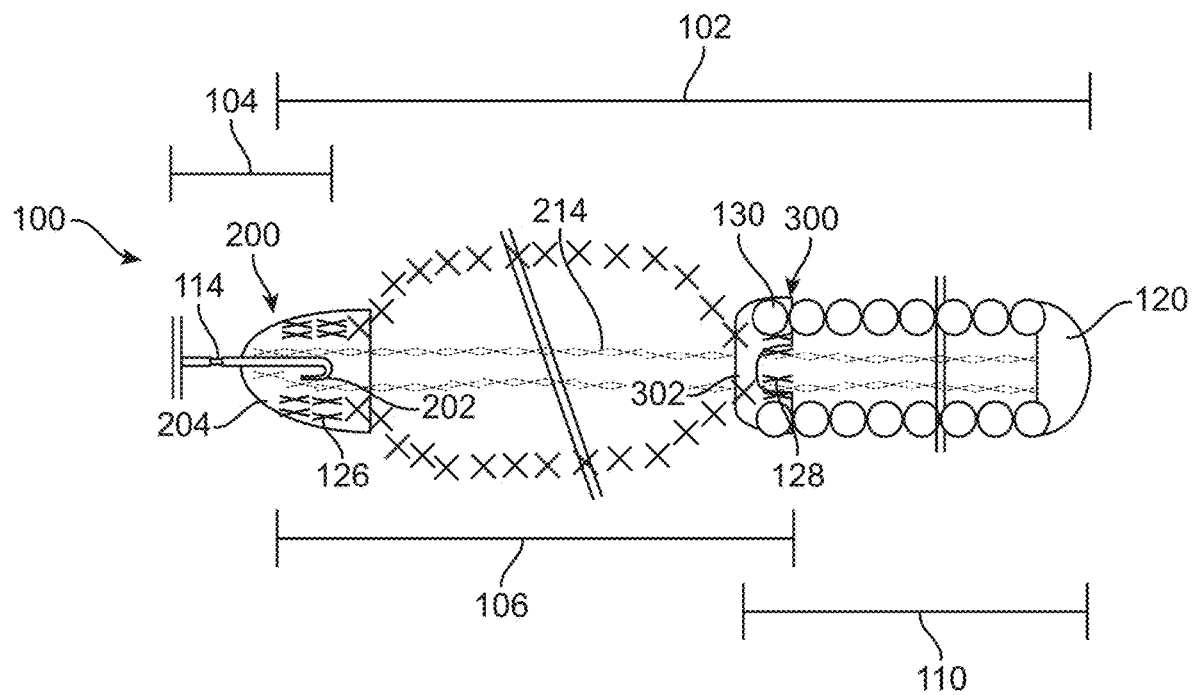

FIG. 11 depicts a vaso-occlusive treatment system 100 according to yet another embodiment. The vaso-occlusive treatment system 100 depicted in FIG. 11 is similar to the vaso-occlusive treatment system 100 depicted in FIG. 10. One difference is that the inner braid 214 extends from the major junction 200, through the intra-device junction 300, and to the distal tip 120 of the distal portion 110 of the vaso-occlusive device 102. The inner braid 214 traverses the entire vaso-occlusive device, and acts as a stretch-resisting member, thereby eliminating the need for a separate stretch-resisting member (a second difference). A third difference is that the hook 202 at the distal end of the delivery assembly 104 may be mechanically coupled to a proximal end of the inner braid 214. The inner braid 214 can be woven from DFT, Pt and/or NiTi wires, as described above. The major junction 200 also includes an adhesive drop 204, which permeates the braided proximal end 126 of central portion 106 of the vaso-occlusive device 102 and binds together: (1) the hook 202 of the delivery assembly 104; (2) a proximal portion of the inner braid 214; and (3) the proximal end 126 of the central portion 106 of the vaso-occlusive device 102, thereby forming the major junction 200. In this embodiment, the inner braid 214 further enhances pushability, reduces kinking of the entire vaso-occlusive device 102, protects both the major junction 200 and the intra-device junction 300, and prevents stretching of the vaso-occlusive device 102 as it is withdrawn proximally during delivery.

While the vaso-occlusive treatment systems 100 depicted in FIGS. 8-11 include various vaso-occlusive devices 102, major junctions 200, and intra-device junctions 300 in various combinations, this disclosure is not intended to be limited by the exemplary vaso-occlusive treatment systems 100. Accordingly, the respective vaso-occlusive devices 102, major junctions 200, and intra-device junctions 300 disclosed herein can be assembled in any reasonable fashion to form different vaso-occlusive treatment systems 100. Also, it will be apparent that some components of the disclosed vaso-occlusive treatment systems 100 need not be present in all vaso-occlusive treatment systems 100.

FIGS. 12-23 depict major junctions 200 according to various embodiments. While the major junctions 200 depicted in FIGS. 12 and 14-23 do not include a stretch-resisting member, they can be modified to include one or more stretch-resisting members. Further, the major junctions 200 can be modified to function as intra-device junctions 300.

Figure 12:
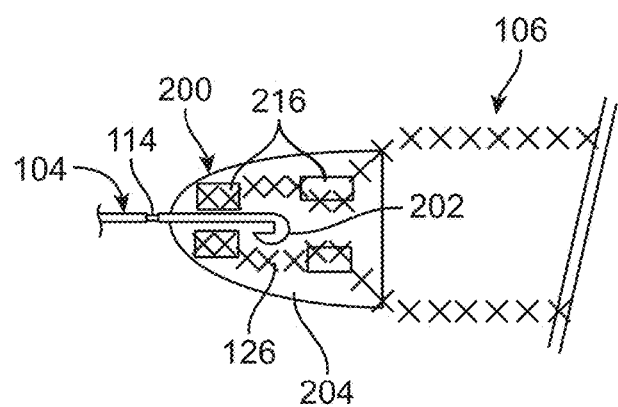
FIGS. 12-22 are longitudinal cross-section views of major junctions constructed according to various disclosed embodiments.

The major junction 200 depicted in FIG. 12 is similar to the one depicted in FIG. 8, except that the major junction 200 depicted in FIG. 12 includes a pair of marker bands 216 surrounding the necked down proximal end 126 of the central portion 106 of the vaso-occlusive device 102. The marker bands 216 reinforce the coupling of the hook 202 (and the delivery assembly 104) and the proximal end 126 of the central portion 106 of the vaso-occlusive device 102, thereby strengthening the major junction 200. The marker bands 216 also maintain the reduced diameter of the necked down proximal end 126. The more proximal marker band 216 also mechanically interferes (e.g., interlocks) with the hook 202 to reinforce the coupling of the hook 202 and the proximal end 126, also strengthening the major junction 200.

Figure 13:
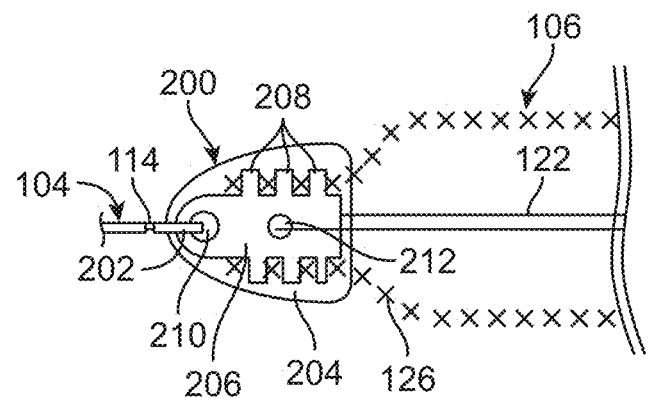

The major junction 200 depicted in FIG. 13 is similar to the one depicted in FIG. 9, except that the vaso-occlusive device 102 partially depicted in FIG. 13 does not include a proximal portion 108. Accordingly, the major junction 200 depicted in FIG. 13 includes a link/adapter 206 and a necked down proximal end 126 of the central portion 106 of the vaso-occlusive device 102. The braid in the necked down proximal end 126 is sufficiently open such that the fingers 208 of the link can pass through the braid in a radial direction. In addition, the portions of the necked down proximal end 126 adjacent to the link 206 may be welded or soldered to the link 206 to reinforce the coupling of the link 206 (and the delivery assembly 104 coupled thereto) and the central portion 106 of the vaso-occlusive device 102.

Figure 14:
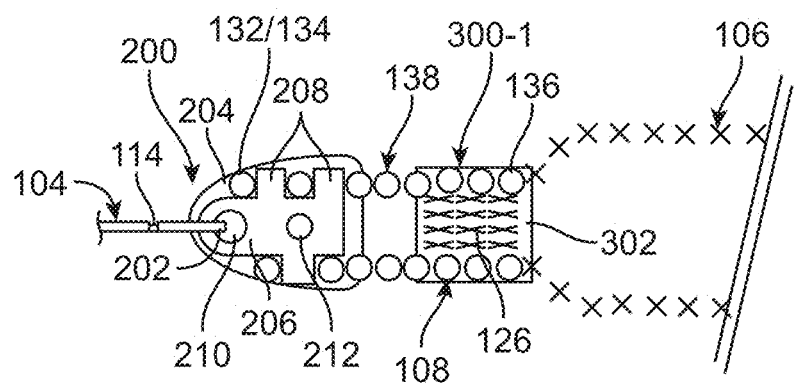

The vaso-occlusive treatment system 100 partially depicted in FIG. 14 is similar to the one depicted in FIG. 9, except that the proximal intra-device junction 300-1 of the vaso-occlusive treatment system 100 partially depicted in FIG. 14 is axially longer than the proximal intra-device junction 300-1 of the vaso-occlusive treatment system 100 depicted in FIG. 9. The proximal intra-device junction 300-1 depicted in FIG. 14 includes an open distal end 136 of the proximal portion 108 of the vaso-occlusive device 102, a necked down proximal end 126 of the central portion 106 of the vaso-occlusive device 102, and an adhesive drop 302. The necked down proximal end 126 of the central portion 106 includes an extended length of the braid disposed inside of the distal end 136 of the proximal portion 108, thereby lengthening the proximal intra-device junction 300-1. The area of the proximal portion 108 (i.e., coil) of the vaso-occlusive device 102 between the major junction 200 and the proximal intra-device junction 300-1 forms an articulation portion 138 configured to facilitate bending of the vaso-occlusive device 102.

Figure 15:
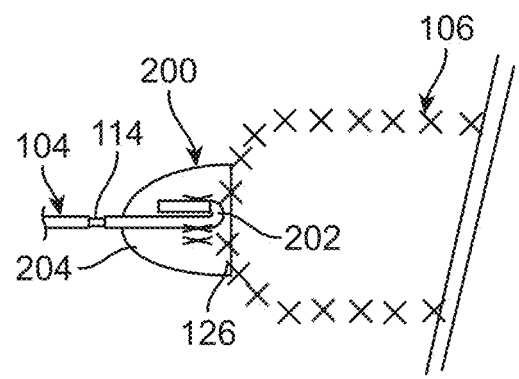

The major junction 200 depicted in FIG. 15 is similar to the one depicted in FIG. 8, except that the necked down proximal end 126 of the central portion 106 of the vaso-occlusive device 102 depicted in FIG. 15 is reduced in diameter until the sides of the braid abut, thereby mechanically interfering with the hook 202. This modification of the necked down proximal end 126 reinforces the coupling of the hook 202 and the proximal end 126. The hook 202 and the proximal end 126 can be further joined by laser welding, soldering or with an adhesive drop.

Figure 16:
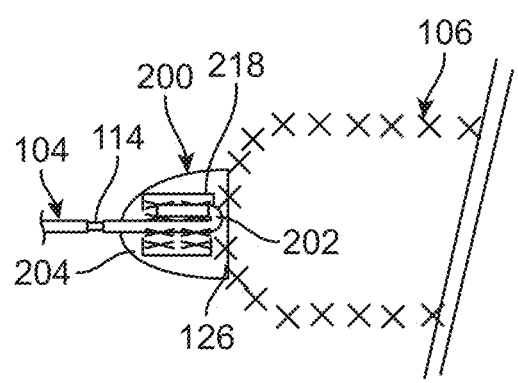

The major junction 200 depicted in FIG. 16 is similar to the one depicted in FIG. 15, except that the major junction 200 depicted in FIG. 16 includes a lamination layer 218 surrounding the necked down proximal end 126 of the central portion 106 of the vaso-occlusive device 102. The lamination layer 218 reinforces the coupling of the hook 202 (and the delivery assembly 104) and the proximal end 126 of the central portion 106 of the vaso-occlusive device 102. The lamination layer 218 also maintains the reduced diameter of the necked down proximal end 126.

Figure 17:
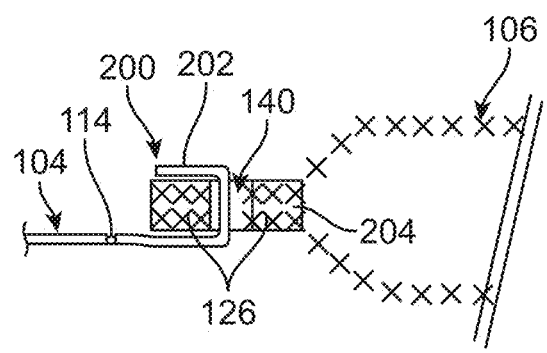

The major junction 200 depicted in FIG. 17 is similar to the one depicted in FIG. 8, except that the braid in the necked down proximal end 126 of the central portion 106 of the vaso-occlusive device 102 depicted in FIG. 17 is partially open to define an aperture 140. The hook 202 formed at the distal end of the delivery assembly 104 passes through the aperture 140, thereby coupling the hook 202 and the proximal end 126.

Figure 18:
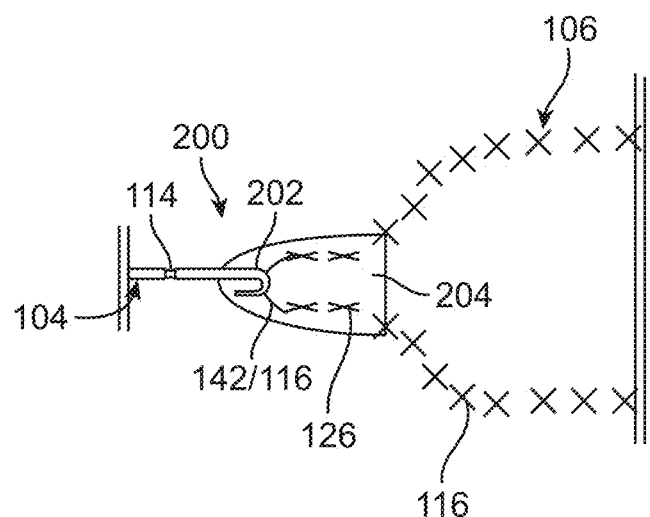

The major junction 200 depicted in FIG. 18 is similar to the one depicted in FIG. 8, except that the braid in the necked down proximal end 126 of the central portion 106 of the vaso-occlusive device 102 depicted in FIG. 18 forms a proximal loop 142. The proximal loop 142 can be formed from one or more elongate members 116 from which the central portion 106 is braided. The hook 202 formed at the distal end of the delivery assembly 104 passes through the proximal loop 142, thereby coupling the hook 202 and the proximal end 126. The major junction 200 also includes an adhesive drop 204, which couples the hook 202 of the delivery assembly 104 and the proximal loop 142 formed at the proximal end 126 of the central portion 106 of the vaso-occlusive device 102.

Figure 19:
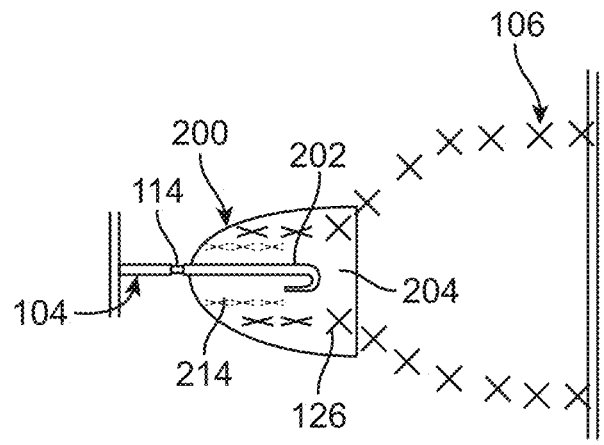

The major junction 200 depicted in FIG. 19 is similar to the one depicted in FIG. 10, except that the inner braid 214 is shorter and does not extend over the hook 202. The inner braid 214 is still disposed radially between the distal end of the delivery assembly 104 and the necked down proximal end 126 of the central portion 106 of the vaso-occlusive device 102. The inner braid 214 mechanically interferes (e.g., interlocks) with the hook 202. The inner braid 214 can be woven from DFT, Pt and/or NiTi wires, as described above. The major junction 200 also includes an adhesive drop 204, which permeates the braided proximal end 126 of central portion 106 of the vaso-occlusive device 102 and binds together: (1) the hook 202 of the delivery assembly 104; (2) a proximal portion of the inner braid 214; and (3) the proximal end 126 of the central portion 106 of the vaso-occlusive device 102, thereby forming the major junction 200. The inner braid 214 reinforces the coupling of the hook 202 and the proximal end 126. The inner braid 214 also enhances pushability, reduces kinking of the central portion 106 (particularly at the major junction 200), and protects and strengthens the major junction 200.

Figure 20:
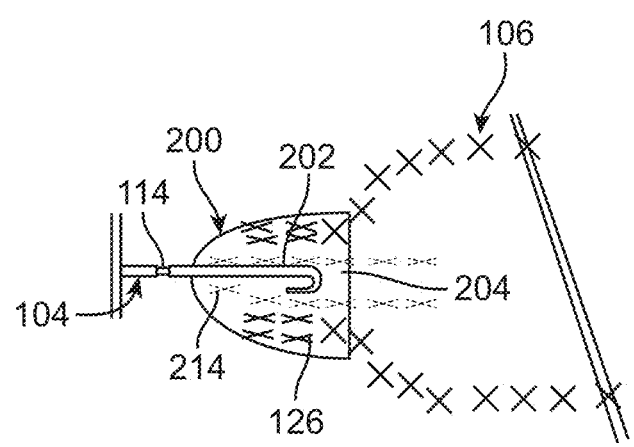

The major junction 200 depicted in FIG. 20 is almost identical to the one depicted in FIG. 10, except that the major junction 200 depicted in FIG. 20 does not include a stretch-resisting member. Therefore, the adhesive drop 204 in the major junction 200 binds together: (1) the hook 202 of the delivery assembly 104; (2) a proximal portion of the inner braid 214; and (3) the proximal end 126 of the central portion 106 of the vaso-occlusive device 102, thereby forming the major junction 200. The inner braid 214 reinforces the coupling of the hook 202 and the proximal end 126. The inner braid 214 also enhances pushability, reduces kinking of the central portion 106 (particularly at the major junction 200), and protects and strengthens the major junction 200.

Figure 21:
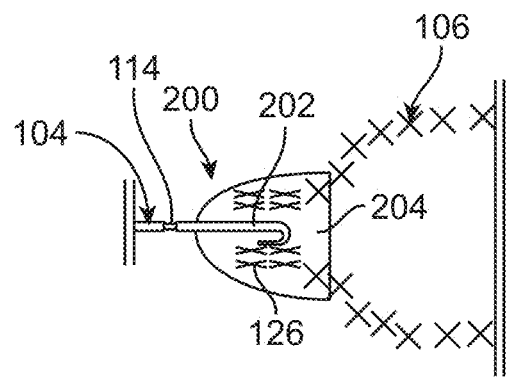

The major junction 200 depicted in FIG. 21 is almost identical to the one depicted in FIG. 8, except that the major junction 200 depicted in FIG. 21 does not include a stretch-resisting member. The hook 202 mechanically interferes (e.g., interlocks) with the necked down the proximal end 126 of the central portion 106 of the vaso-occlusive device 102 to strengthen the major junction 200. Therefore, the adhesive drop 204 in the major junction 200 binds together: (1) the hook 202 of the delivery assembly 104; and (2) the proximal end 126 of the central portion 106 of the vaso-occlusive device 102, thereby forming the major junction 200.

Figure 22:
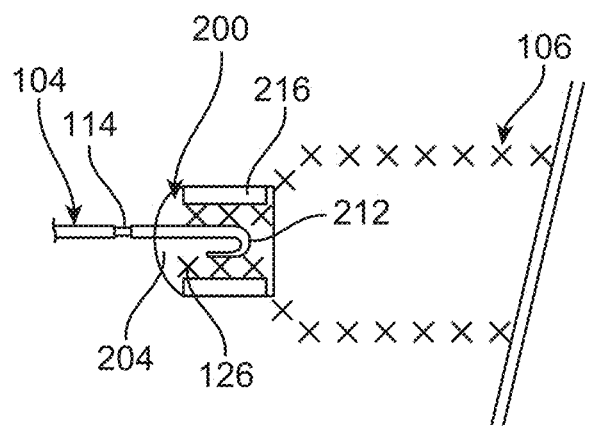

The major junction 200 depicted in FIG. 22 is similar to the one depicted in FIG. 12, except that the major junction 200 depicted in FIG. 22 includes one instead of two marker bands 216. The marker band 216 surrounds the necked down proximal end 126 of the central portion 106 of the vaso-occlusive device 102. The marker bands 216 reinforce the coupling of the hook 202 (and the delivery assembly 104) and the proximal end 126 of the central portion 106 of the vaso-occlusive device 102, thereby strengthening the major junction 200. The marker band 216 also maintains the reduced diameter of the necked down proximal end 126.

Figure 23:
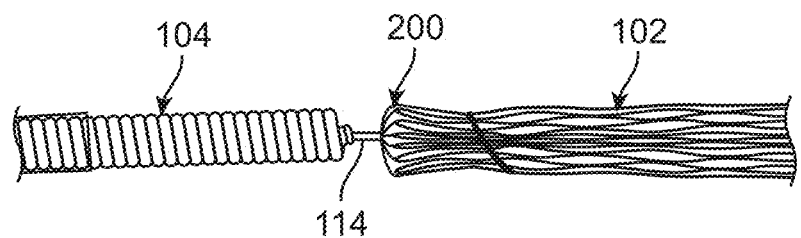
FIGS. 23, 32 and 37 are photographs of respective major junctions employed in vaso-occlusive device delivery systems constructed according to various disclosed embodiments.

FIG. 23 generally depicts a major junction 200 coupling a delivery assembly 104 and a central portion 106 of a vaso-occlusive device 102 according to one embodiment. The major junction 200 depicted in FIG. 23 can be similar or identical to the ones depicted in FIGS. 8, 10-13 and 15-22, because the adhesive drop 204 obscures the details of the major junction 200.

FIGS. 24-51 depict intra-device junctions 300 according to various embodiments. While specific intra-device junctions 300 depicted in 24-51 either include or not include a stretch-resisting member, they can be modified to not include or include one or more stretch-resisting members. Further, the intra-device junctions 300 can be modified to function as major junctions 200. Moreover, while the intra-device junctions 300 depicted in 24-51 couple a central portion 106 to a distal portion 110, they can be modified to couple a central portion 106 to a proximal portion 108.

Figure 24:
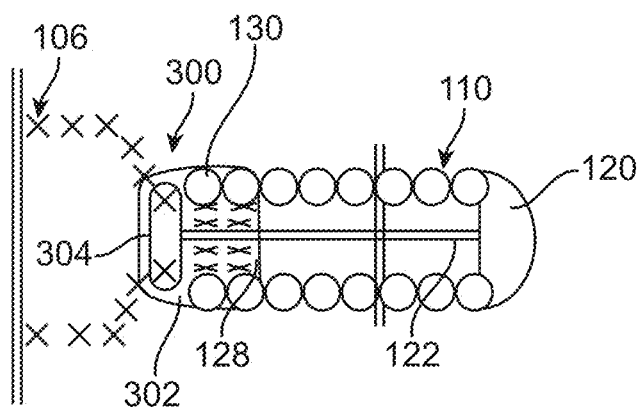
FIGS. 24-31, 33, 35, 36, 38, 39 and 41-45 are longitudinal cross-section views of alternative intra-device junctions constructed according to various disclosed embodiments.

The intra-device junction 300 depicted in FIG. 24 is similar to the one depicted in FIG. 8. One difference is that the stretch-resisting member 122 ends immediately proximal of the intra-device junction 300 in a loop 304 instead of extending all the way to the major junction 200. The loop 304 encircles portions of the braid forming the distal end 128 of the central portion 106 of the vaso-occlusive device 102, thereby anchoring the proximal end of the stretch-resisting member 122. The stretch-resisting member 122 extends from proximal of the intra-device junction 300 to the atraumatic distal tip 120, and reduces elongation of the distal portion 110 of the vaso-occlusive device 102 as it is withdrawn proximally during delivery. The stretch-resisting member 122 couples the central and distal portions 106, 110 of the vaso-occlusive device 102. The intra-device junction 300 also includes an adhesive drop 302, which binds together: (1) the distal end 128 of the central portion 106 of the vaso-occlusive device 102; (2) the stretch-resisting member 122; (3) the loop 304; and (4) the open proximal end 130 of the distal portion 110 of the vaso-occlusive device 102, thereby forming the intra-device junction 300 and coupling the central and distal portions 106, 110 of the vaso-occlusive device 102.

Figure 25:
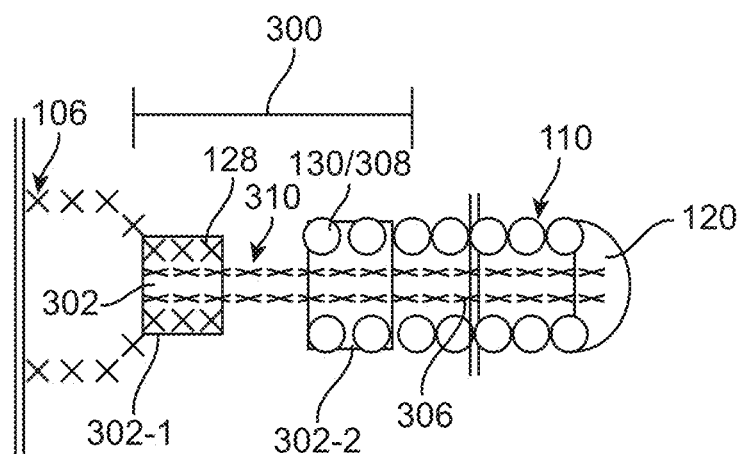

The intra-device junction 300 depicted in FIG. 25 is similar to the one depicted in FIG. 8, with one difference being that the intra-device junction 300 depicted in FIG. 25 includes a DFT braid 306, which acts as a stretch-resisting member. As such, the intra-device junction 300 depicted in FIG. 25 does not include a stretch-resisting member such as the one depicted in FIG. 8. The DFT braid 306 extends from the intra-device junction 300 to the atraumatic distal tip 120, and reduces elongation of the distal portion 110 of the vaso-occlusive device 102 as it is withdrawn proximally during delivery. While the DFT braid 306 shown in FIG. 25 terminates at the intra-device junction 300, in other embodiments, the DFT braid 306 can extend proximally all the way to the major junction 200. The DFT braid 306 couples the central and distal portions 106, 110 of the vaso-occlusive device 102. The intra-device junction 300 also includes proximal and distal adhesive drops 302-1, 302-2. The proximal adhesive drop 302-1 penetrates the necked down distal end 128 of the braided central portion 106, and binds together the proximal end of the DFT braid 306 and the necked down distal end 128 of the central portion 106. The distal adhesive drop 302-2 penetrates open pitch windings 308 at the proximal end 130 of the coiled distal portion 110, and binds together a middle portion of the DFT braid 306 and the proximal end 130 of the distal portion 110. The portion of the DFT braid 306 between the proximal and distal adhesive drops 302-1, 302-2 form an articulation portion 310 configured to facilitate bending of the vaso-occlusive device 102.

Figure 26:
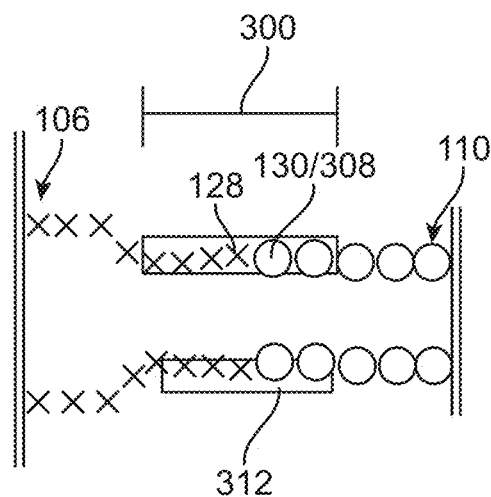

The intra-device junction 300 depicted in FIG. 26 is similar to the one depicted in FIG. 8, except that the distal end 128 of the central portion 106 is necked down less than the one in FIG. 8. Instead of necking down the distal end 128 so that it fits inside of the open proximal end 130 of distal portion 110, the distal end 128 of the central portion 106 is necked down so that its diameter is substantially the same as the diameter of the proximal end 130 of the distal portion 110. Also, the intra-device junction 300 depicted in FIG. 25 includes a tube 312 (e.g., a PET tube), which is melted onto (and into) and couples the central and distal portions 106, 110 of the vaso-occlusive device 102. The tube 312 penetrates open pitch windings 308 at the proximal end 130 of the coiled distal portion 110 and the braid at the distal end 128 of the central portion 106 to more securely couple the central and distal portions 106, 110 together.

Figure 27:
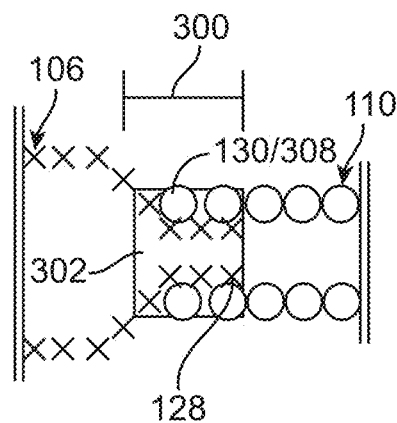

The intra-device junction 300 depicted in FIG. 27 is similar to the one depicted in FIG. 8, one difference being that the intra-device junction 300 does not include a stretch-resisting member. The adhesive drop 302 penetrates open pitch windings 308 at the proximal end 130 of the coiled distal portion 110 and the braid at the distal end 128 of the central portion 106. The adhesive drop 302 binds together the distal end 128 of the central portion 106 of the vaso-occlusive device 102 and the open proximal end 130 of the distal portion 110 of the vaso-occlusive device 102, thereby forming the intra-device junction 300 and coupling the central and distal portions 106, 110 of the vaso-occlusive device 102.

Figure 28:
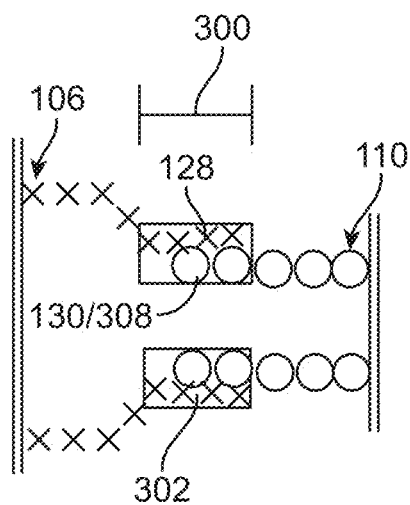

The intra-device junction 300 depicted in FIG. 28 is similar to the one depicted in FIG. 8, with one difference being that the distal end 128 of the central portion 106 is necked down less than the one in FIG. 8. Instead of necking down the distal end 128 so that it fits inside of the open proximal end 130 of distal portion 110, the distal end 128 of the central portion 106 is necked down so that its diameter is slightly larger than the diameter of the proximal end 130 of the distal portion 110. Also, instead of the distal end 128 of the central portion 106 being disposed in the proximal end 130 of the distal portion 110, the proximal end 130 of the distal portion 110 is disposed in the distal end 128 of the central portion 106. Further, the intra-device junction 300 does not include a stretch-resisting member. The adhesive drop 302 penetrates the braid at the distal end 128 of the central portion 106 and open pitch windings 308 at the proximal end 130 of the coiled distal portion 110. The adhesive drop 302 binds together the distal end 128 of the central portion 106 of the vaso-occlusive device 102 and the open proximal end 130 of the distal portion 110 of the vaso-occlusive device 102, thereby forming the intra-device junction 300 and coupling the central and distal portions 106, 110 of the vaso-occlusive device 102.

Figure 29:
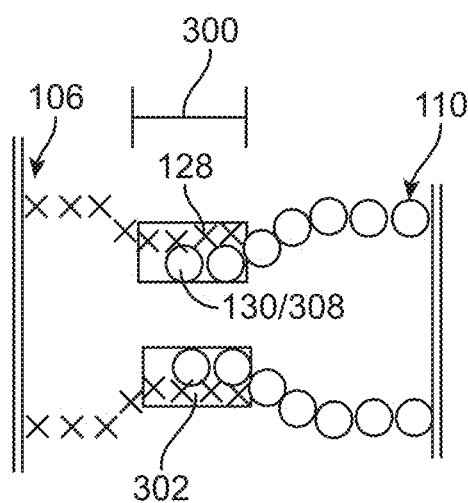

The intra-device junction 300 depicted in FIG. 29 is similar to the one depicted in FIG. 28, except that, in addition to the necked down distal end 128 of the central portion 106, the proximal end 130 of the distal portion 110 is also necked down. The distal end 128 of the central portion 106 and the proximal end 130 of the distal portion 110 are necked down such that the diameter of the distal end 128 of the central portion 106 is slightly larger than the diameter of the proximal end 130 of the distal portion 110. This allows the proximal end 130 of the distal portion 110 to be disposed in the distal end 128 of the central portion 106. Therefore, when the vaso-occlusive device 102 is pushed distally during delivery, the distal end 128 of the central portion 106 pushes against the proximal end 130 of the distal portion 110, transmitting force distally. Further, the intra-device junction 300 does not include a stretch-resisting member. The adhesive drop 302 penetrates the braid at the distal end 128 of the central portion 106 and open pitch windings 308 at the proximal end 130 of the coiled distal portion 110. The adhesive drop 302 binds together the distal end 128 of the central portion 106 of the vaso-occlusive device 102 and the open proximal end 130 of the distal portion 110 of the vaso-occlusive device 102, thereby forming the intra-device junction 300 and coupling the central and distal portions 106, 110 of the vaso-occlusive device 102.

Figure 30:
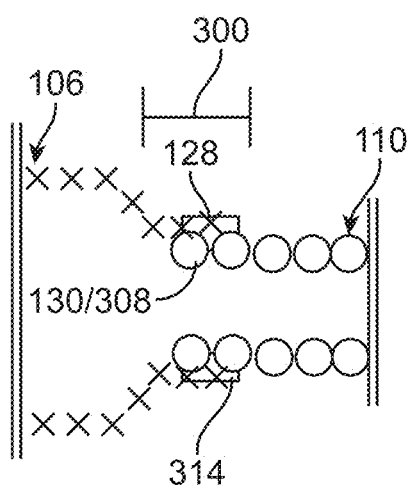

The intra-device junction 300 depicted in FIG. 30 is similar to the one depicted in FIG. 28. One difference is that, instead of binds together the distal end 128 of the central portion 106 and the proximal end 130 of the distal portion 110 with an adhesive drop, the central and distal portions 106, 110 are welded (e.g., laser welded) together. As shown in FIG. 30, a weld 314 couples the distal end 128 of the central portion 106 and the proximal end 130 of the distal portion 110. The weld 314 strengthen the intra-device junction 300.

Figure 31:
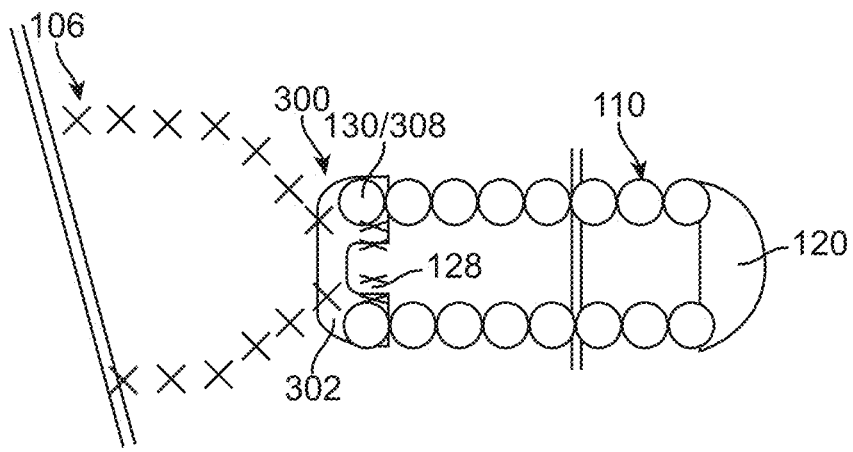

The intra-device junction 300 depicted in FIG. 31 is similar to the one depicted in FIG. 9, except that the intra-device junction 300 does not include a stretch-resisting member. The adhesive drop 302 penetrates open pitch windings 308 at the proximal end 130 of the coiled distal portion 110 and the braid at the distal end 128 of the central portion 106. The adhesive drop 302 binds together the distal end 128 of the central portion 106 of the vaso-occlusive device 102 and the open proximal end 130 of the distal portion 110 of the vaso-occlusive device 102, thereby forming the intra-device junction 300 and coupling the central and distal portions 106, 110 of the vaso-occlusive device 102.

Figure 33:
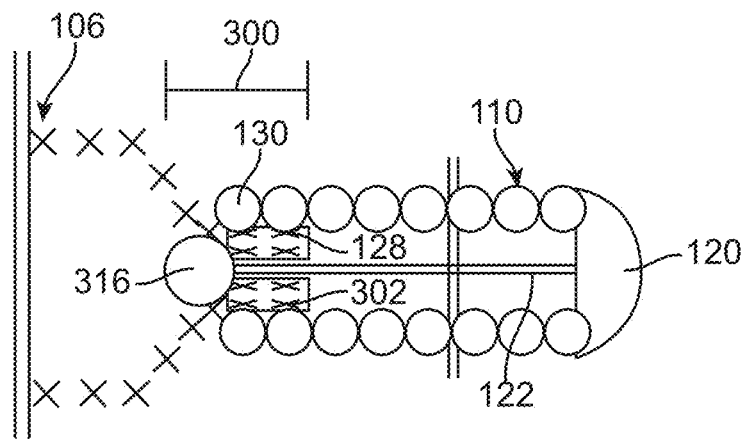

The intra-device junction 300 depicted in FIG. 33 is similar to the one depicted in FIG. 8, one difference being that the stretch-resisting member 122 ends immediately proximal of the intra-device junction 300 in an enlargement 316 instead of extending all the way to the major junction 200. The stretch-resisting member 122 extends from proximal of the intra-device junction 300 to the atraumatic distal tip 120, and reduces elongation of the distal portion 110 of the vaso-occlusive device 102 as it is withdrawn proximally during delivery. The stretch-resisting member 122 couples the central and distal portions 106, 110 of the vaso-occlusive device 102. The intra-device junction 300 also includes an adhesive drop 302, which binds together: (1) the necked down distal end 128 of the central portion 106 of the vaso-occlusive device 102; (2) the stretch-resisting member 122 passing through the distal end 128; and (3) the enlargement 316.

Figure 34:
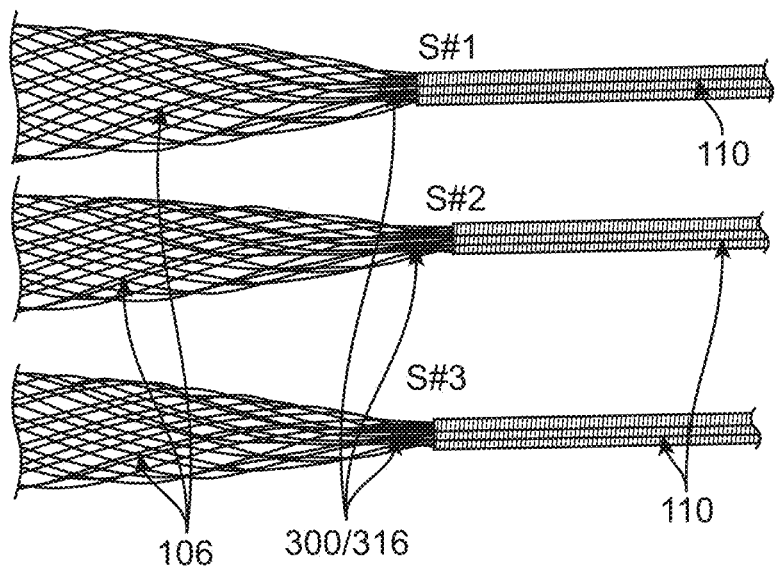
FIG. 34 is a photograph of three intra-device junctions according to one embodiment, which is similar to the intra-device junction depicted in FIG. 33.

FIG. 34 generally depicts three intra-device junctions 300 coupling respective central and distal portions 106, 110 of a vaso-occlusive device 102 according to one embodiment. The intra-device junctions 300 depicted in FIG. 34 are similar or identical to the one depicted in FIG. 33. An enlargement 316 formed at the proximal end of the stretch-resisting member 122 is visible in each of the three intra-device junctions 300.

Figure 35:
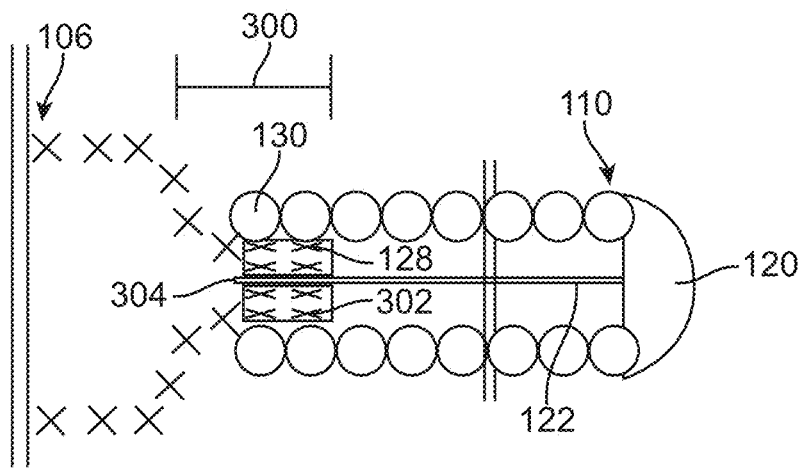

The intra-device junction 300 depicted in FIG. 35 is similar to the one depicted in FIG. 24. One difference is that the adhesive drop 302 only impregnates the necked down distal end 128 of the central portion 106 of the vaso-occlusive device 102, instead of the entire intra-device junction 300. The stretch-resisting member 122 ends immediately proximal of the intra-device junction 300 in a loop 304, which encircles portions of the braid forming the distal end 128 of the central portion 106 of the vaso-occlusive device 102, thereby anchoring the proximal end of the stretch-resisting member 122. The stretch-resisting member 122 extends from proximal of the intra-device junction 300 to the atraumatic distal tip 120, and reduces elongation of the distal portion 110 of the vaso-occlusive device 102 as it is withdrawn proximally during delivery. The stretch-resisting member 122 couples the central and distal portions 106, 110 of the vaso-occlusive device 102. The adhesive drop 302 binds together: (1) the distal end 128 of the central portion 106 of the vaso-occlusive device 102; (2) the stretch-resisting member 122; and (3) the loop 304.

Figure 36:
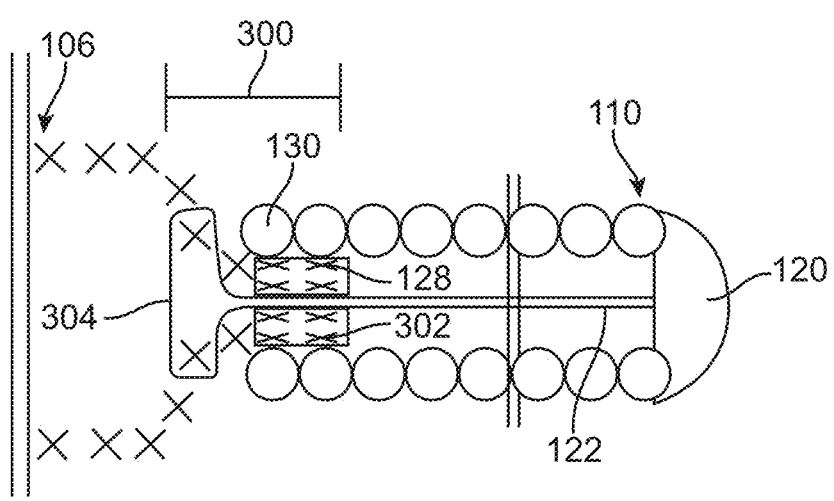

The intra-device junction 300 depicted in FIG. 36 is almost identical to the one depicted in FIG. 24, one difference being that the adhesive drop 302 only impregnates the necked down distal end 128 of the central portion 106 of the vaso-occlusive device 102, instead of the entire intra-device junction 300. The loop 304 (at the proximal end of the stretch-resisting member 122) encircles portions of the braid forming the distal end 128 of the central portion 106 of the vaso-occlusive device 102, thereby anchoring the proximal end of the stretch-resisting member 122. The stretch-resisting member 122 extends from proximal of the intra-device junction 300 to the atraumatic distal tip 120, and reduces elongation of the distal portion 110 of the vaso-occlusive device 102 as it is withdrawn proximally during delivery. The stretch-resisting member 122 couples the central and distal portions 106, 110 of the vaso-occlusive device 102. The adhesive drop 302 binds together: (1) the distal end 128 of the central portion 106 of the vaso-occlusive device 102; and (2) the stretch-resisting member 122.

Figure 38:
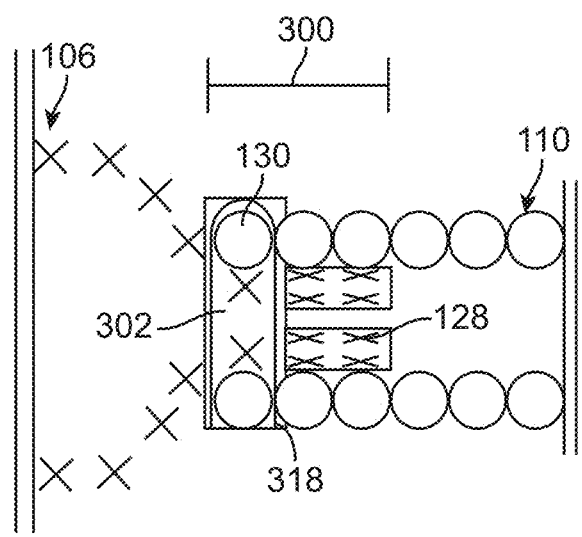

The intra-device junction 300 depicted in FIG. 38 is similar to the one depicted in FIG. 8, one difference being that the intra-device junction 300 does not include a stretch-resisting member. Another difference is that the intra-device junction 300 also includes a "U" shaped locking pin 318. The locking pin 318 passes radially through both (1) the proximal end 130 of the distal portion 110 of the vaso-occlusive device 102 and (2) the necked down distal end 128 of the central portion 106 of the vaso-occlusive device 102, thereby coupling the central and distal portions 106, 110. The locking pin 318 passes through both sides of the central and distal portions 106, 110 to reinforce the coupling. The intra-device junction 300 also includes an adhesive drop 302, which binds together: (1) the distal end 128 of the central portion 106 of the vaso-occlusive device 102; (2) the proximal end 130 of the distal portion 110 of the vaso-occlusive device 102; and (3) the locking pin 318, thereby forming the intra-device junction 300 and coupling the central and distal portions 106, 110 of the vaso-occlusive device 102.

Figure 39:
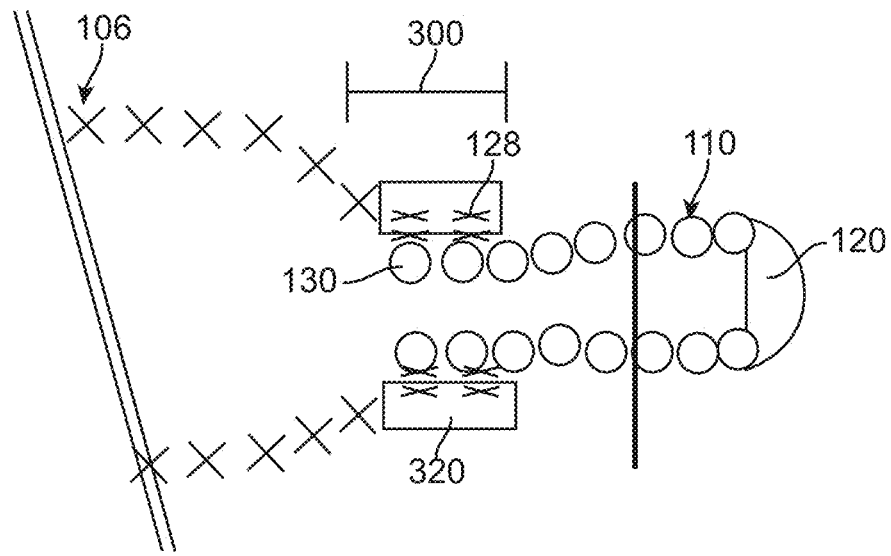

The intra-device junction 300 depicted in FIG. 39 is similar to the one depicted in FIG. 29, except that, instead of an adhesive drop, the intra-device junction 300 depicted in FIG. 39 includes a marker band 320 surrounding the necked down distal end 128 of the central portion 106 and the necked down proximal end 130 of the distal portion 110. A portion of the marker band 320 is laser welded to melt (1) the portion of the mark band 320; (2) a portion of the distal end 128 of the central portion 106; and (3) a portion of the proximal end 130 of the distal portion 110. When these portions cool and solidify, they are coupled together. Further, the distal end 128 of the central portion 106 and the proximal end 130 of the distal portion 110 are necked down such that the diameter of the distal end 128 of the central portion 106 is slightly larger than the diameter of the proximal end 130 of the distal portion 110. This allows the proximal end 130 of the distal portion 110 to be disposed in the distal end 128 of the central portion 106, so that when the vaso-occlusive device 102 is pushed distally during delivery, the distal end 128 of the central portion 106 pushes against the proximal end 130 of the distal portion 110, transmitting force distally.

Figure 40:
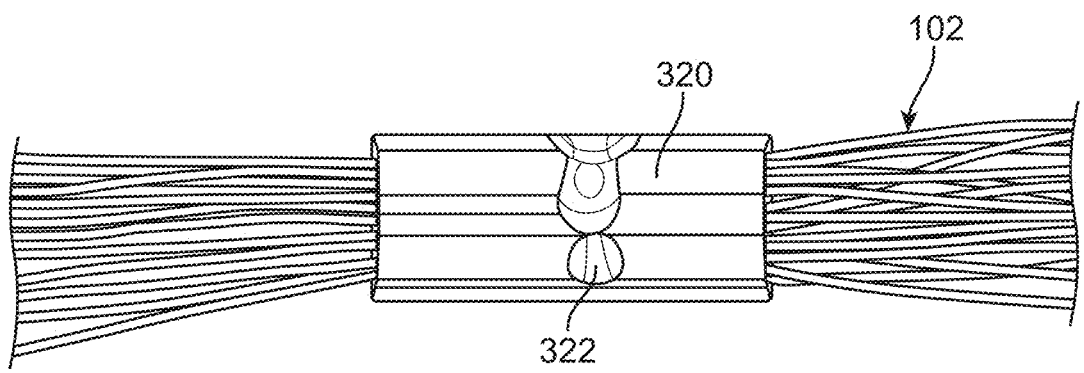
FIG. 40 is a photograph of a braided vaso-occlusive device constructed according to one embodiment.

FIG. 40 generally depicts a marker band 302 disposed around a braided vaso-occlusive device 102, demonstrating that a marker band 302 may be coupled to a braided vaso-occlusive device 102 using laser welding in a manner similar to the laser welded coupling depicted in FIG. 39. FIG. 40 shows a weld spot 322 on the marker band 320, formed by a 15 ms burst of a fiber laser at 33% power. The braided vaso-occlusive device 102 is formed from 16 NiTi filaments, with a 24 picks/in. braid. The outer diameter of the braided vaso-occlusive device 102 is 0.0008 in. The marker band 320 is made from metal with an inner diameter of 0.0085 in., an outer diameter of 0.0105 in., and a length of 0.025 in.

Figure 41:
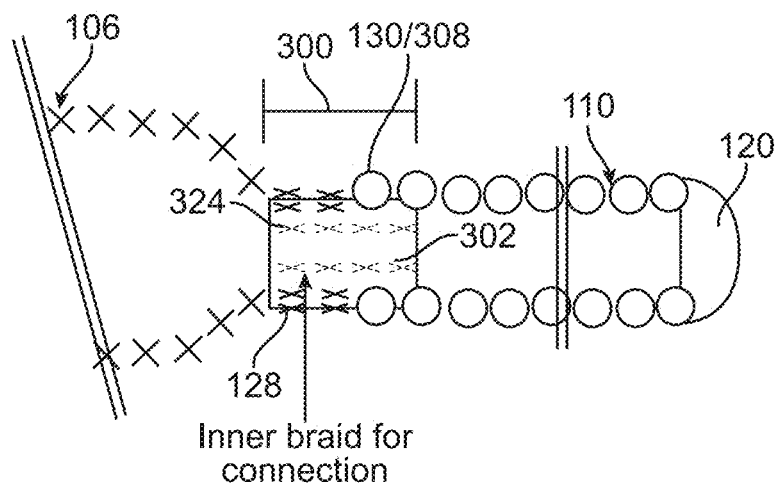

The intra-device junction 300 depicted in FIG. 41 is similar to the one depicted in FIG. 11, one difference being that the inner braid 324 in the intra-device junction 300 does not extend the length of the vaso-occlusive device 102, as does the inner braid 214 in FIG. 11. Another difference is that the distal end 128 of the central portion 106 is necked down less than the one in FIG. 11. Instead of necking down the distal end 128 so that it fits inside of the open proximal end 130 of the distal portion 110, the distal end 128 of the central portion 106 is necked down so that its diameter is substantially the same as the diameter of the proximal end 130 of the distal portion 110. The inner braid 324 underlies both the distal end 128 of the central portion 106 and the proximal end 130 of the distal portion 110. The intra-device junction 300 also includes an adhesive drop 302, which permeates the braided distal end 128 of central portion 106 of the vaso-occlusive device 102 and open pitch windings 308 at the proximal end 130 of the coiled distal portion 110. The adhesive drop 302 binds together: (1) the distal end 128 of the central portion 106; (2) the proximal end 130 of the coiled distal portion 110; and (3) the inner braid 324, thereby forming the intra-device junction 300. The inner braid 324 enhances pushability, reduces kinking of the central portion 106 (particularly at the intra-device junction 300), and protects and strengthens the intra-device junction 300.

Figure 42:
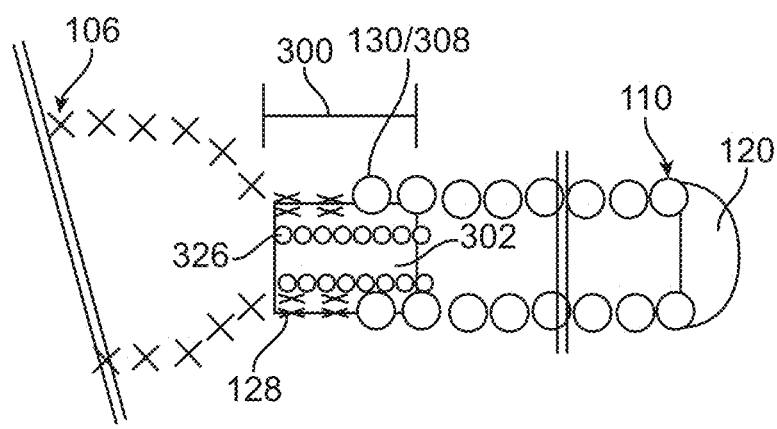

The intra-device junction 300 depicted in FIG. 42 is almost identical to the one depicted in FIG. 41, except that the inner braid 324 depicted in FIG. 41 has been replaced with an inner coil 326 in FIG. 42. The amount of necking down of the distal end 128 of the central portion 106 and the adhesive drop 302 are substantially identical between the intra-device junctions 300 depicted in FIGS. 41 and 42. The inner coil 326 enhances pushability, reduces kinking of the central portion 106 (particularly at the intra-device junction 300), and protects and strengthens the intra-device junction 300.

Figure 43:
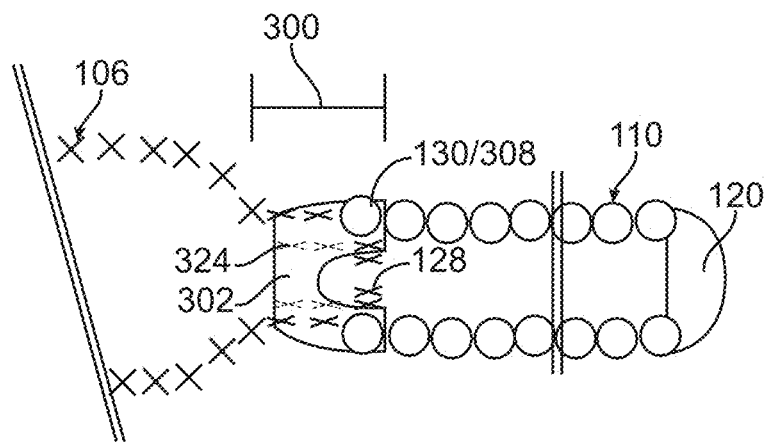

The intra-device junction 300 depicted in FIG. 43 is almost identical to the one depicted in FIG. 11, except that the inner braid 324 in the intra-device junction 300 does not extend the length of the vaso-occlusive device 102, as does the inner braid 214 in FIG. 11. The inner braid 324 enhances pushability, reduces kinking of the central portion 106 (particularly at the intra-device junction 300), and protects and strengthens the intra-device junction 300.

Figure 44:
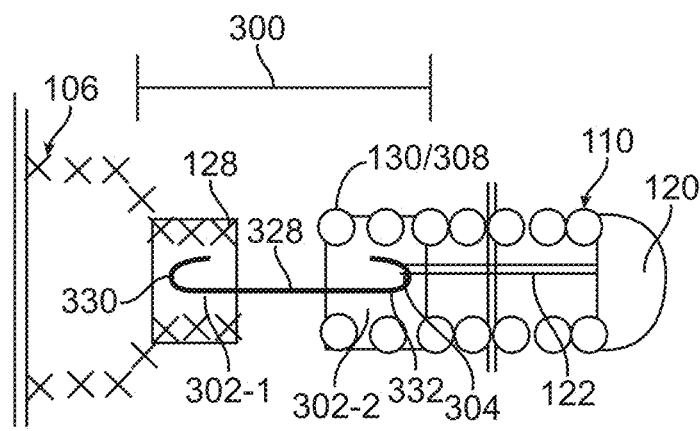

The intra-device junction 300 depicted in FIG. 44 is similar to the one depicted in FIG. 25, except that the DFT braid 306 depicted in FIG. 25 is replaced with a wire 328 and a stretch-resisting member 122. Another difference is that the intra-device junction 300 also includes proximal and distal adhesive drops 302-1, 302-2. The wire 328 has a proximal hook 330 and a distal hook 332. The proximal hook 330 is coupled to the necked down distal end 128 of the central portion 106 by the proximal adhesive drop 302-1. The distal hook 332 passes through a loop 304 formed at a proximal end of the stretch-resisting member 122, thereby coupling the wire 328 to the distal portion 110 of the vaso-occlusive device 102. The distal adhesive drop 302-2 penetrates open pitch windings 308 at the proximal end 130 of the coiled distal portion 110, and binds together: (1) the distal end of the wire 328 (including the distal hook 332); (2) the proximal end of the stretch-resisting member 122; and (3) the proximal end 130 of the distal portion 110. The proximal adhesive drop 302-1 penetrates the necked down distal end 128 of the braided central portion 106, and binds together the proximal end of the wire 328 (including the proximal hook 330) and the necked down distal end 128 of the central portion 106. The portion of the wire 328 between the proximal and distal adhesive drops 302-1, 302-2 form an articulation portion 310 configured to facilitate bending of the vaso-occlusive device 102.

Figure 45:
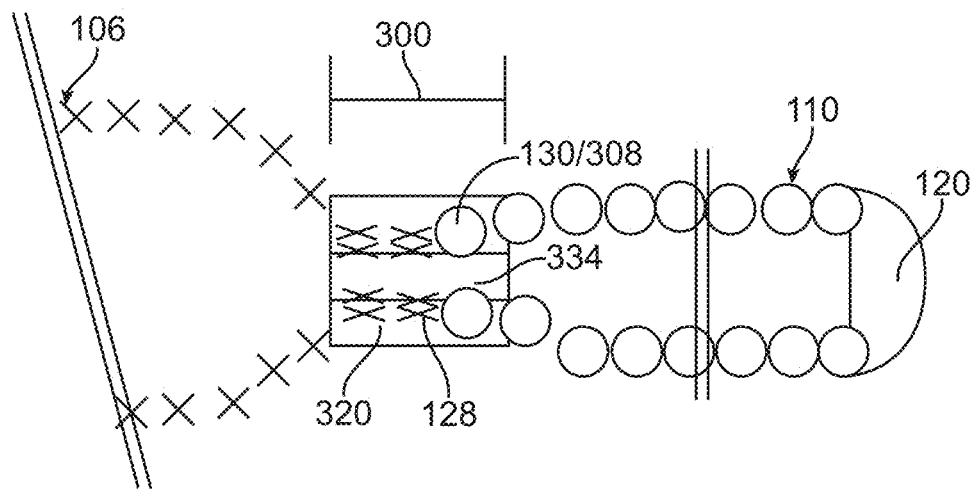

The intra-device junction 300 depicted in FIG. 45 is similar to the one depicted in FIG. 41, one difference being that the inner braid 324 depicted in FIG. 41 is replaced with a solid support 334 (e.g., a Pt rod) in FIG. 45. Another difference is that the adhesive drop 302 depicted in FIG. 41 is replaced with a crimped marker band 320 in FIG. 45. Assembling the intra-device junction 300 depicted in FIG. 45 can begin by inserting the solid support 334 half way into the open proximal end 130 of a coiled distal portion 110. Then a distal end 128 of the braided central portion 106 can be placed over the exposed half of the solid support 334. Next, the marker band 320 can be placed over portions of the central and distal portions 106, 110 overlying the solid support 334. Finally, the marker band 320 is crimped to mechanically bond the marker band 320, portions of the central and distal portions 106, 110, and the solid support 334 to form the intra-device junction 300. The solid support 334 and the marker band 320 enhance pushability, reduce kinking of the central portion 106 (particularly at the intra-device junction 300), and protect and strengthen the intra-device junction 300.

Figure 46:
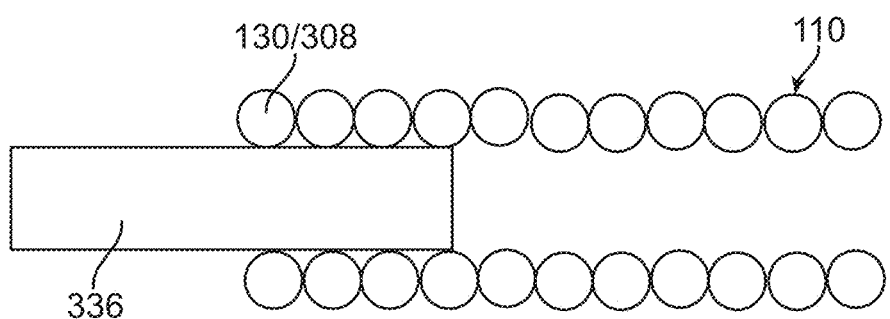
FIGS. 46-49 are longitudinal cross-section views of components of vaso-occlusive treatment system during a an exemplary manufacturing process according to the disclosed embodiments.
Figure 47:
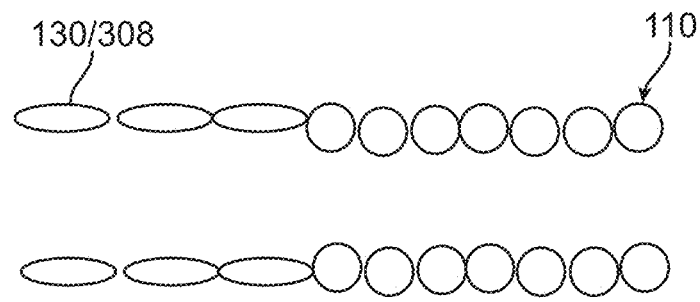
Figure 48:
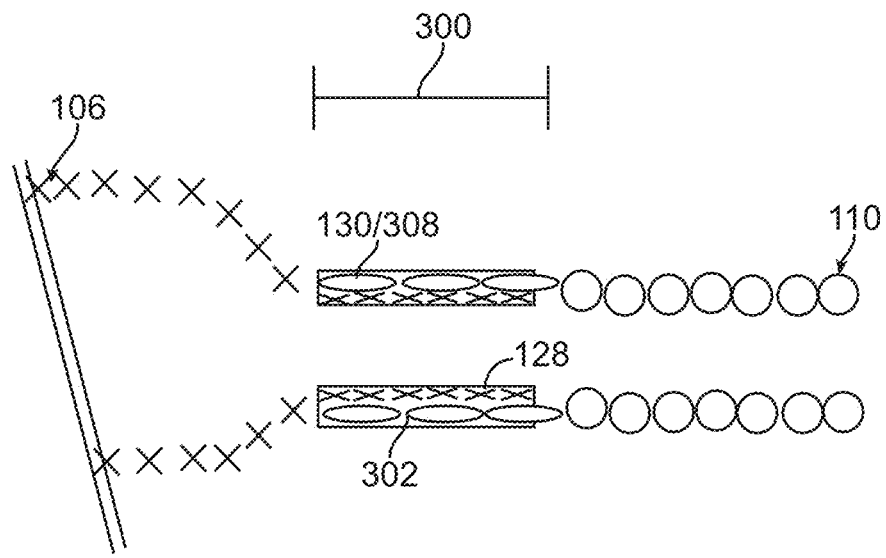

FIGS. 46-49 depict methods of forming an intra-device junction 300, according to two embodiments. FIG. 46 depicts a mandrel 336 inserted into the open proximal end 130 of a coiled distal portion 110. Next the windings 308 at the proximal end 130 of the distal portion 110 are swaged against the mandrel 336 from a circular cross-section to an elliptical cross-section, while retaining the same outer coil diameter, as shown in FIG. 47. Next, a necked down distal end 128 of the central portion 106 is inserted into the swaged proximal end 130 of the distal portion 110. The elliptical cross-section of the windings 308 results in a larger contact area between the central and distal portions 106, 110. Finally, the overlapping central and distal portions 106, 110 are coupled with an adhesive drop 302, as shown in FIG. 48.

Figure 49:
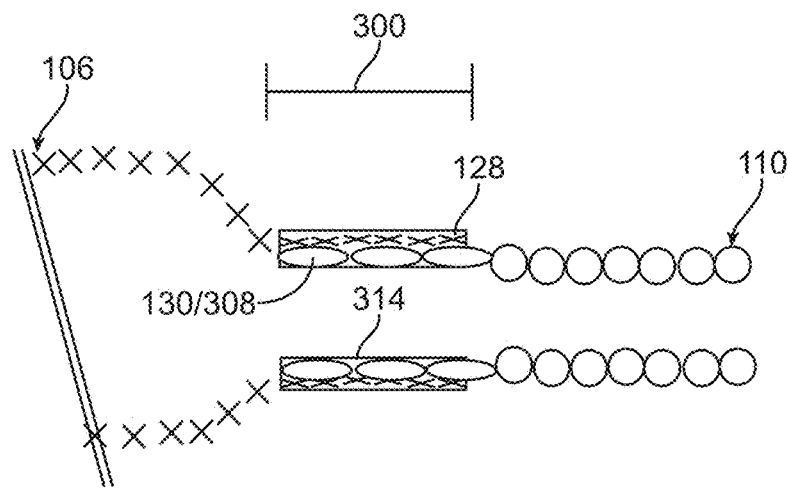

In an alternative embodiment, the distal end 128 of the central portion 106 is necked down such that its diameter is slightly larger than the diameter of the swaged proximal end 130 of the distal portion 110. After swaging, the swaged proximal end 130 of the distal portion 110 is inserted into the necked down distal end 128 of the central portion 106. The elliptical cross-section of the windings 308 results in a larger contact area between the central and distal portions 106, 110. Then, the overlapping central and distal portions 106, 110 are coupled with a laser weld 314, as shown in FIG. 49.

Figure 32:
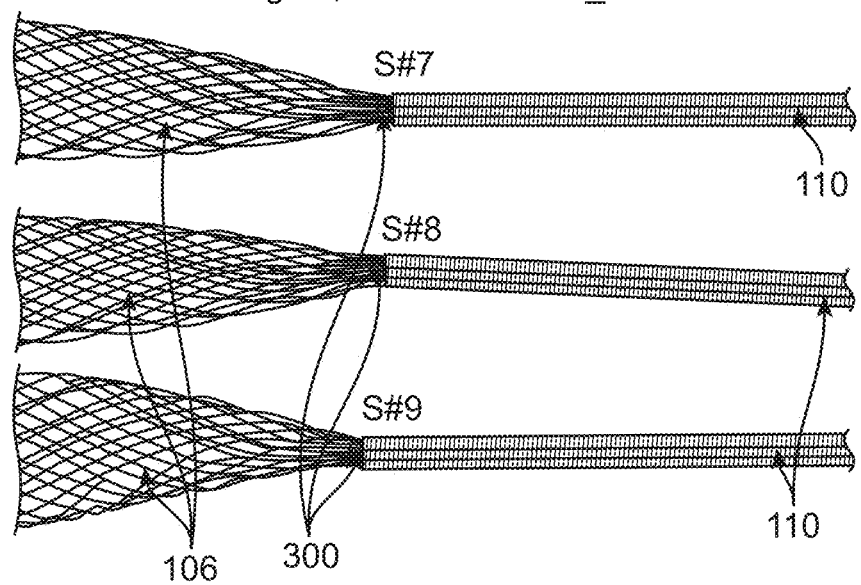
Figure 37:
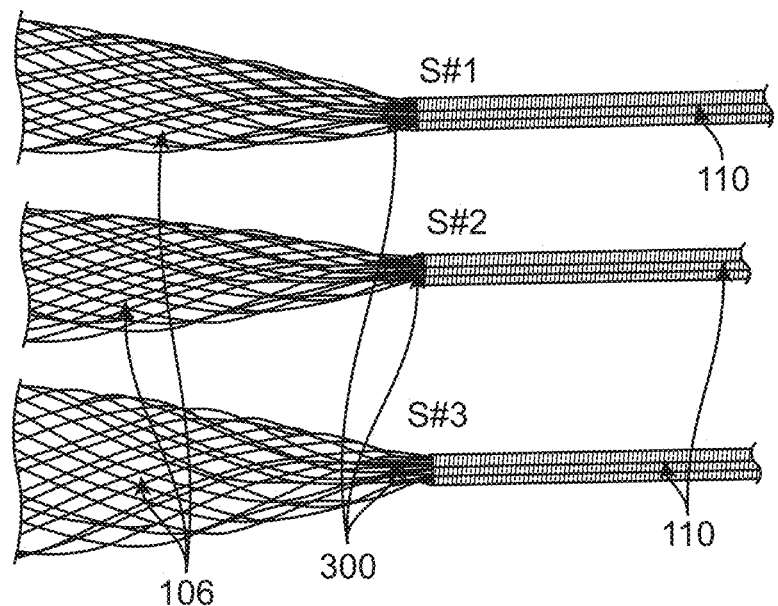

FIGS. 32 and 37 generally depict intra-device junctions 300 coupling central and distal portions 106, 110 of a vaso-occlusive device 102 according to various embodiments. The intra-device junctions 300 depicted in FIGS. 32 and 37 can be similar or identical to the ones depicted in FIGS. 8-11, 24-31, 33, 35, 36, 38 and 41-49, because the adhesive drops 302 obscures the details of the respective intra-device junctions 300.

Figure 50:
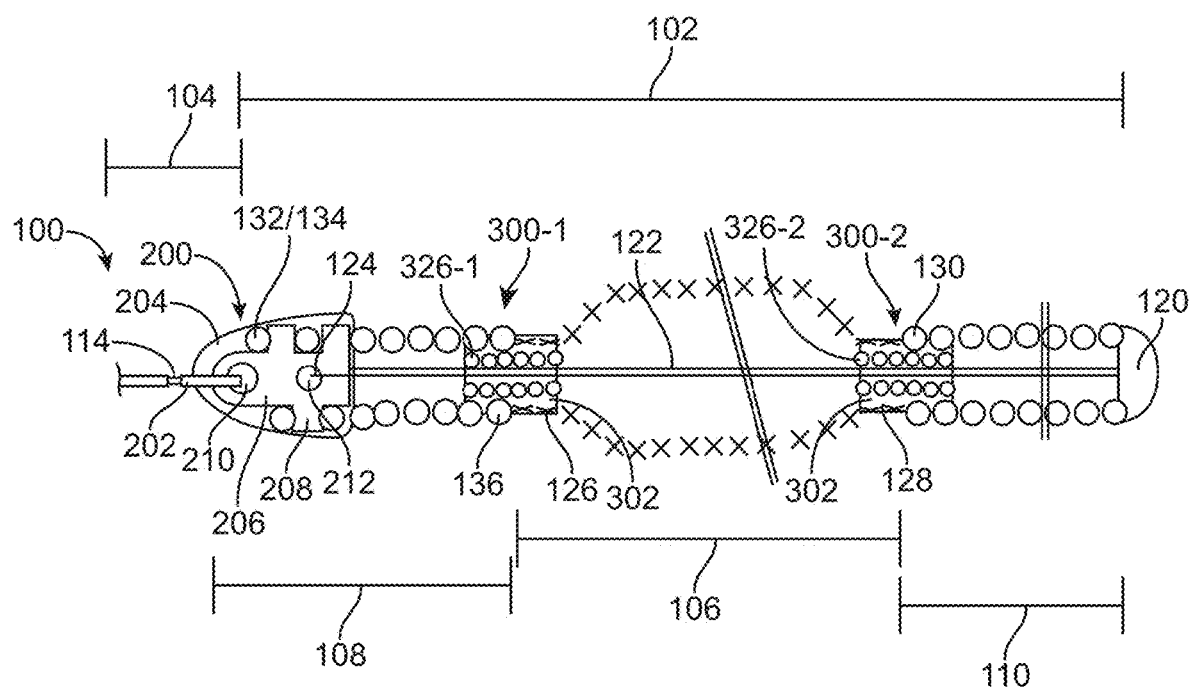
FIG. 50 is a longitudinal cross-section view of an exemplary vaso-occlusive treatment system, including a vaso-occlusive device and a delivery assembly, constructed according to the disclosed embodiments.

The vaso-occlusive treatment system 100 depicted in FIG. 50 is similar to the one depicted in FIG. 9, except that the proximal and distal intra-device junctions 300-1, 300-2 include respective proximal and distal inner coils 326-1, 326-2. The structure and function of the proximal and distal inner coils 326-1, 326-2 are similar to the inner coil depicted in FIG. 42 and described above. However, because the vaso-occlusive device 102 depicted in FIG. 50 include a stretch-resisting member 122 that runs the length of the vaso-occlusive device 102, the proximal and distal inner coils 326-1, 326-2 perform the additional function of centering the stretch-resisting member 122 and providing a smooth transition for same. The proximal and distal inner coils 326-1, 326-2 also enhance pushability, reduce kinking of the central portion 106 (particularly at the proximal and distal intra-device junctions 300-1, 300-2), and protect and strengthen the proximal and distal intra-device junctions 300-1, 300-2.

Figure 51:
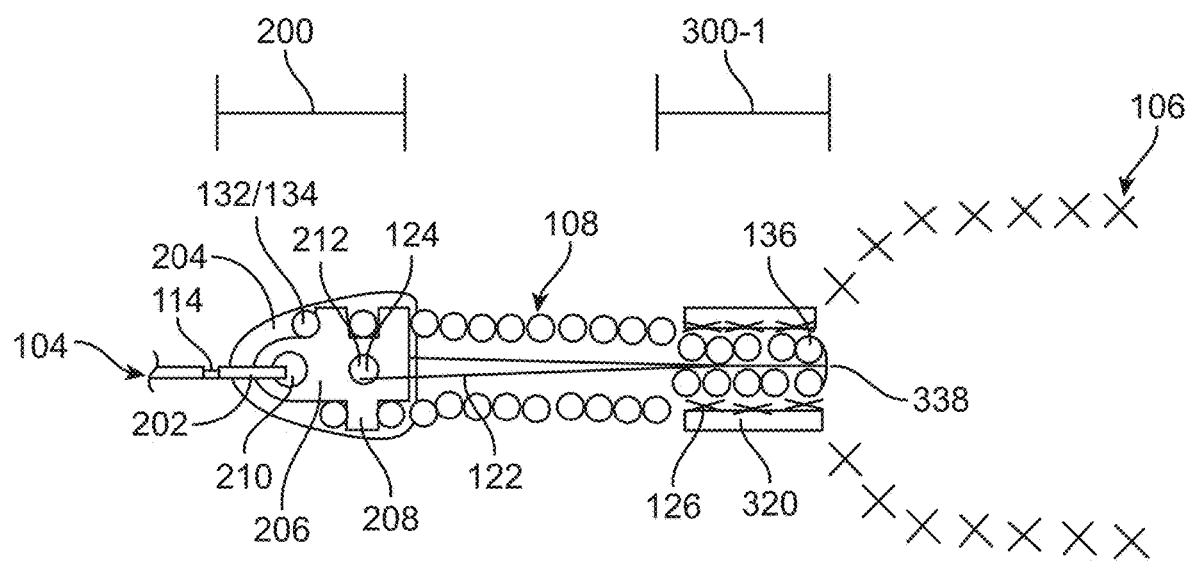
FIGS. 51-56 are longitudinal cross-section views of portions of vaso-occlusive treatment systems, each including a major junction and an intra-device junction, constructed according to various disclosed embodiments.

The vaso-occlusive treatment system 100 partially depicted in FIG. 51 is similar to the one depicted in FIG. 50. One difference is that the proximal intra-device junction 300-1 depicted in FIG. 51 does not include a proximal inner coil 326-1. Instead the distal end 136 of the coiled proximal portion 108 is necked down to fit inside of the open proximal end 126 of the central portion 106. Further, the stretch-resisting member 122 does not extend distally past the proximal intra-device junction 300-1. The stretch-resisting member 122 has a proximal loop 124, which passes through the proximal aperture 210 in the link 206, coupling the stretch-resisting member 122 to the link 206, like in the system 100 depicted in FIG. 50. Unlike the system 100 depicted in FIG. 50, the distal end of the stretch-resisting member 122 forms two distal hooks 338 disposed just distal of the distal end 136 of the coiled proximal portion 108. The distal hooks 338 are prevented from moving proximally by mechanical interference from the necked down distal end 136 of the coiled proximal portion 108, thereby anchoring the distal end of the stretch-resisting member 122. The stretch-resisting member 122 is made from DFT or NiTi wire to facilitate formation of distal hooks 338 with sufficient strength to anchor the distal end of the stretch-resisting member 122.

The proximal intra-device junction 300-1 also includes a marker band 320, which is crimped down over the proximal end 126 of the central portion 106, the distal end 136 of the coiled proximal portion 108, and stretch-resisting member 122, thereby forming the proximal intra-device junction 300-1 and coupling the central and distal portions 106, 110 of the vaso-occlusive device 102.

Figure 52:
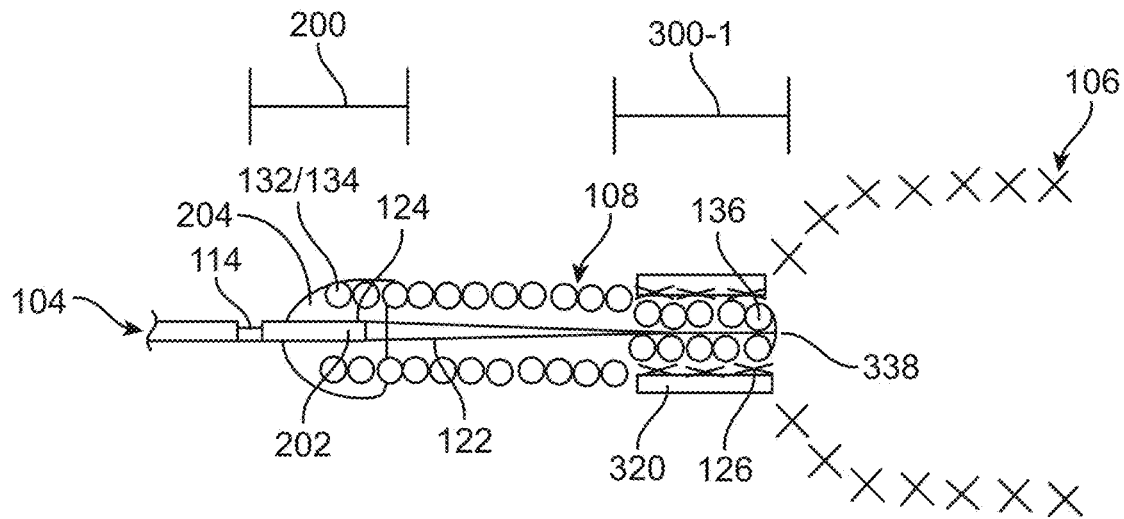

The vaso-occlusive treatment system 100 partially depicted in FIG. 52 is almost identical to the one depicted in FIG. 51, one difference being that the major junction 200 depicted in FIG. 52 does not include a link. Instead, the major junction 200 includes a hook 202 formed at the distal end of the delivery assembly 104, which pass through a loop 124 formed at the proximal end of the stretch-resisting member 122, thereby mechanically coupling the delivery assembly 104 and the stretch-resisting member 122. FIG. 52 depicts the system 100 rotated approximately 90 degrees from the orientation as the system 100 depicted in FIG. 8, such that view is orthogonal to the plane of hook 202, which appears as a line in FIG. 52.

While not shown in FIGS. 51 and 52, the distal end of the vaso-occlusive device 102 may include a coiled distal portion, with a distal intra-device junction having a distal stretch-resisting member anchored similarly to the stretch-resisting member 122 depicted in FIGS. 51 and 52.

Figure 53:
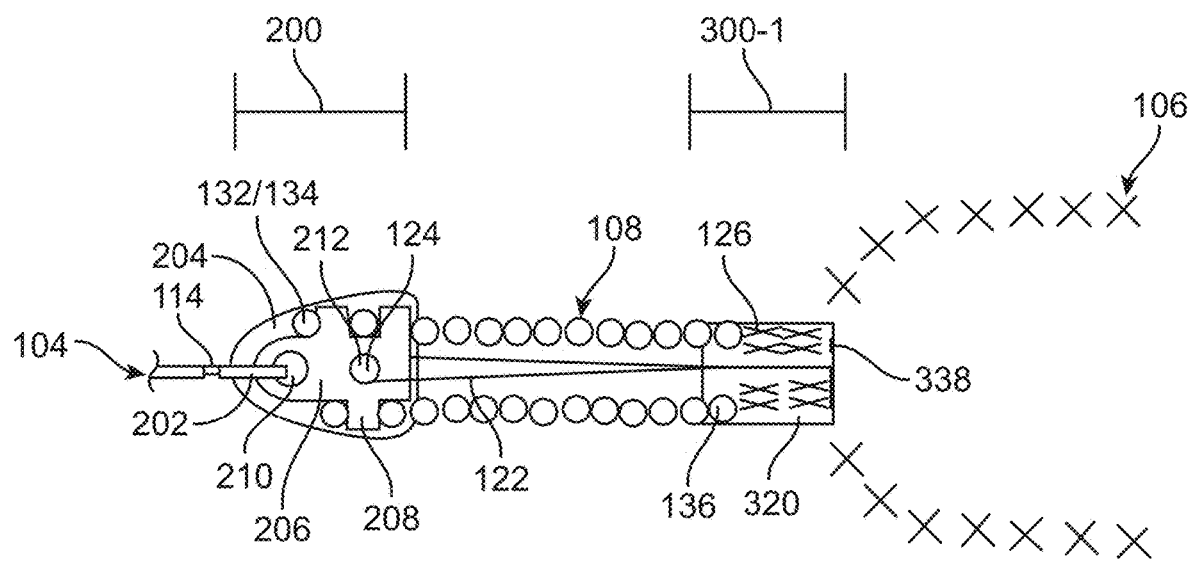

The vaso-occlusive treatment system 100 partially depicted in FIG. 53 is similar to the one depicted in FIG. 50, except that the proximal intra-device junction 300-1 depicted in FIG. 53 does not include a proximal inner coil 326-1. Another difference is that the stretch-resisting member 122 does not extend distally past the proximal intra-device junction 300-1. Instead, the stretch-resisting member 122 has a proximal loop 124, which passes through the proximal aperture 210 in the link 206, coupling the stretch-resisting member 122 to the link 206, like in the system 100 depicted in FIG. 50. Unlike the system 100 depicted in FIG. 50, the distal end of the stretch-resisting member 122 forms two distal hooks 338 disposed just distal of the distal end 136 of the distal end of the necked down proximal end 126 of the central portion 106. The distal hooks 338 are prevented from moving proximally by mechanical interference from the necked down proximal end 126 of the central portion 106, thereby anchoring the distal end of the stretch-resisting member 122. The stretch-resisting member 122 is made from DFT or NiTi wire to facilitate formation of distal hooks 338 with sufficient strength to anchor the distal end of the stretch-resisting member 122.

The proximal intra-device junction 300-1 also includes an adhesive drop 302, which binds together: (1) the distal end 136 of the coiled proximal portion 108; (2) the proximal end 126 of the central portion 106 of the vaso-occlusive device 102; (3) the distal portion of the stretch-resisting member 122; and (4) the hooks 338, thereby forming the proximal intra-device junction 300-1 and coupling the central and distal portions 106, 110 of the vaso-occlusive device 102.

Figure 54:
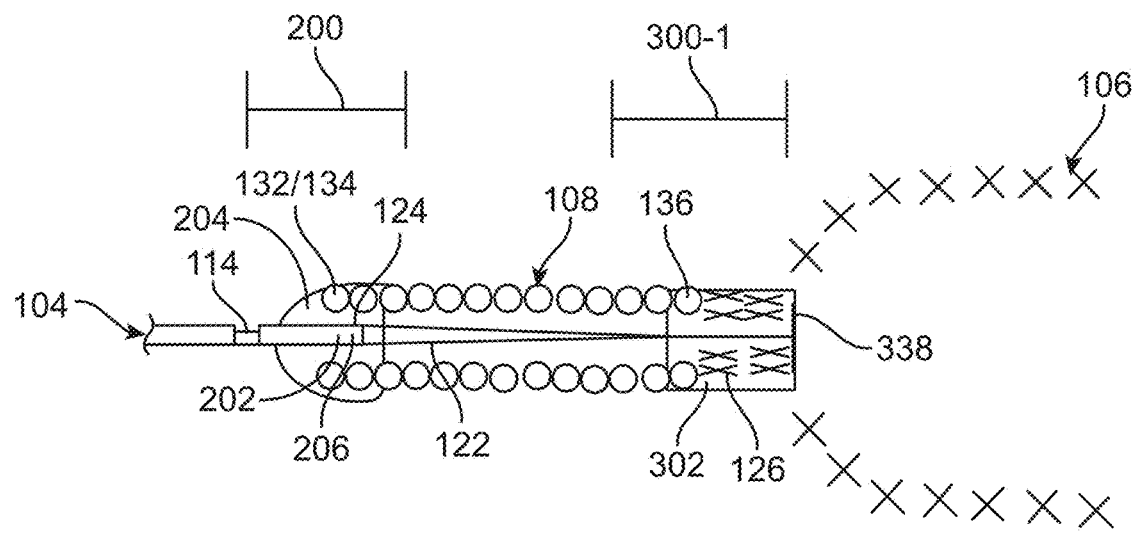

The vaso-occlusive treatment system 100 partially depicted in FIG. 54 is almost identical to the one depicted in FIG. 53, one difference being that the major junction 200 depicted in FIG. 54 does not include a link. Instead, the major junction 200 includes a hook 202 formed at the distal end of the delivery assembly 104, which pass through a loop 124 formed at the proximal end of the stretch-resisting member 122, thereby mechanically coupling the delivery assembly 104 and the stretch-resisting member 122. FIG. 54 depicts the system 100 rotated approximately 90 degrees from the orientation as the system 100 depicted in FIG. 8, such that view is orthogonal to the plane of hook 202, which appears as a line in FIG. 54.

While not shown in FIGS. 53 and 54, the distal end of the vaso-occlusive device 102 may include a coiled distal portion, with a distal intra-device junction having a distal stretch-resisting member anchored similarly to the stretch-resisting member 122 depicted in FIGS. 53 and 54.

Figure 55:
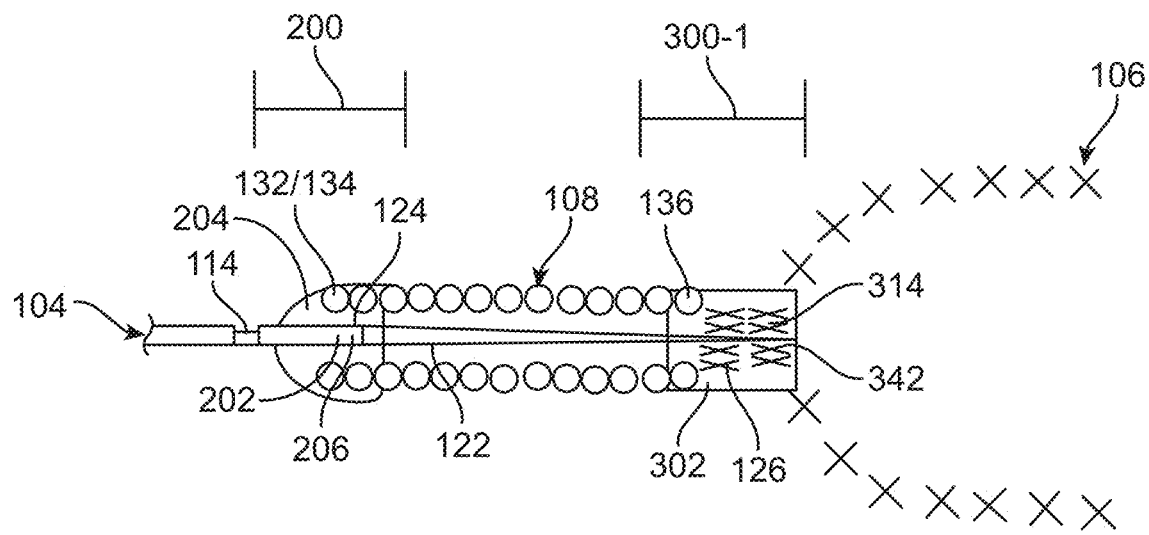

The vaso-occlusive treatment system 100 partially depicted in FIG. 55 is similar to the one partially depicted in FIG. 54, except that the proximal intra-device junction 300-1 also includes a weld 314 (e.g. formed by a laser), which further secures the necked down proximal end 126 of the central portion 106 of the vaso-occlusive device 102 together. Further, the stretch-resisting member 122 does not extend distally past the proximal intra-device junction 300-1. The stretch-resisting member 122 has a proximal loop 124, which passes through the hook 202 formed at the distal end of the delivery assembly 104, coupling the stretch-resisting member 122 to the delivery assembly 104, like in the system 100 depicted in FIG. 54. Unlike the system 100 depicted in FIG. 54, the distal end of the stretch-resisting member 122 forms a distal loop 342 (instead of a hook) disposed around the necked down and welded proximal end 126 of the central portion 106 of the vaso-occlusive device 102. The distal loop 342 is prevented from moving proximally by mechanical interference from the necked down and welded proximal end 126 of the central portion 106, thereby anchoring the distal end of the stretch-resisting member 122. The stretch-resisting member 122 is made from DFT or NiTi wire to facilitate formation of the distal loop 342 with sufficient strength to anchor the distal end of the stretch-resisting member 122.

The proximal intra-device junction 300-1 also includes an adhesive drop 302, which binds together: (1) the distal end 136 of the coiled proximal portion 108; (2) the proximal end 126 of the central portion 106 of the vaso-occlusive device 102; (3) the distal portion of the stretch-resisting member 122; and (4) the distal loop 342, thereby forming the proximal intra-device junction 300-1 and coupling the central and distal portions 106, 110 of the vaso-occlusive device 102. While not shown in FIG. 55, the distal end of the vaso-occlusive device 102 may include a coiled distal portion, with a distal intra-device junction having a distal stretch-resisting member anchored similarly to the stretch-resisting member 122 depicted in FIG. 55.

Figure 56:
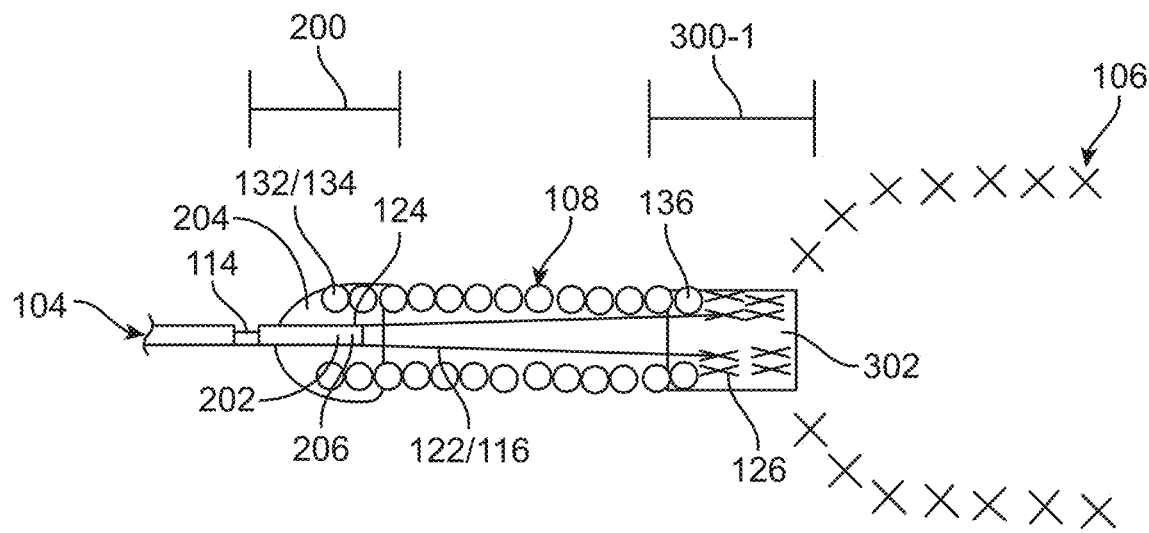

The vaso-occlusive treatment system 100 partially depicted in FIG. 56 is similar to the one partially depicted in FIG. 54, one difference being that the stretch-resisting member 122 depicted in FIG. 56 is made from an elongate member 116, the other end of which is braided with other braid wires to form the central portion 106 of the vaso-occlusive device 102. The other braid wires are trimmed at or adjacent to the proximal intra-device junction 300-1 to leave the elongate member 116 to act as a stretch-resisting member 122. The stretch-resisting member 122 has a proximal loop 124, which passes through the hook 202 formed at the distal end of the delivery assembly 104, coupling the stretch-resisting member 122 to the delivery assembly 104, like in the system 100 depicted in FIG. 54. In the system 100 depicted in FIG. 56, the proximal loop 124 is welded to the hook 202 to further secure these two components of the major junction 200.

The proximal intra-device junction 300-1 also includes an adhesive drop 302, which binds together: (1) the distal end 136 of the coiled proximal portion 108; (2) the proximal end 126 of the central portion 106 of the vaso-occlusive device 102; and (3) the distal portion of the stretch-resisting member 122/the elongate member 116, thereby forming the proximal intra-device junction 300-1 and coupling the central and distal portions 106, 110 of the vaso-occlusive device 102. While not shown in FIG. 56, the distal end of the vaso-occlusive device 102 may include a coiled distal portion, with a distal intra-device junction having a distal stretch-resisting member anchored similarly to the stretch-resisting member 122 depicted in FIG. 56.

While not shown in FIGS. 51-56, the distal ends of the respective vaso-occlusive devices 102 may include coiled distal portions, with distal intra-device junctions having distal stretch-resisting members anchored similarly to the stretch-resisting member 122 depicted in any of FIGS. 51-56.

The adhesive drops 204, 302 described herein can be shaped by placing a polymer (e.g., PET) tube over the adhesive drop 204, 302 and a portion of a vaso-occlusive treatment system 100 on a mandrel before the adhesive is set. Then the tube is heat shrunk to shape the adhesive drop 204, 302. While adhesive drops 204, 302 are used in various embodiments described herein, other substances and techniques can be used to join respective parts. For instance, laser welding and soldering may be used to join parts of the vaso-occlusive treatment systems 100 described herein.

Figure 57:
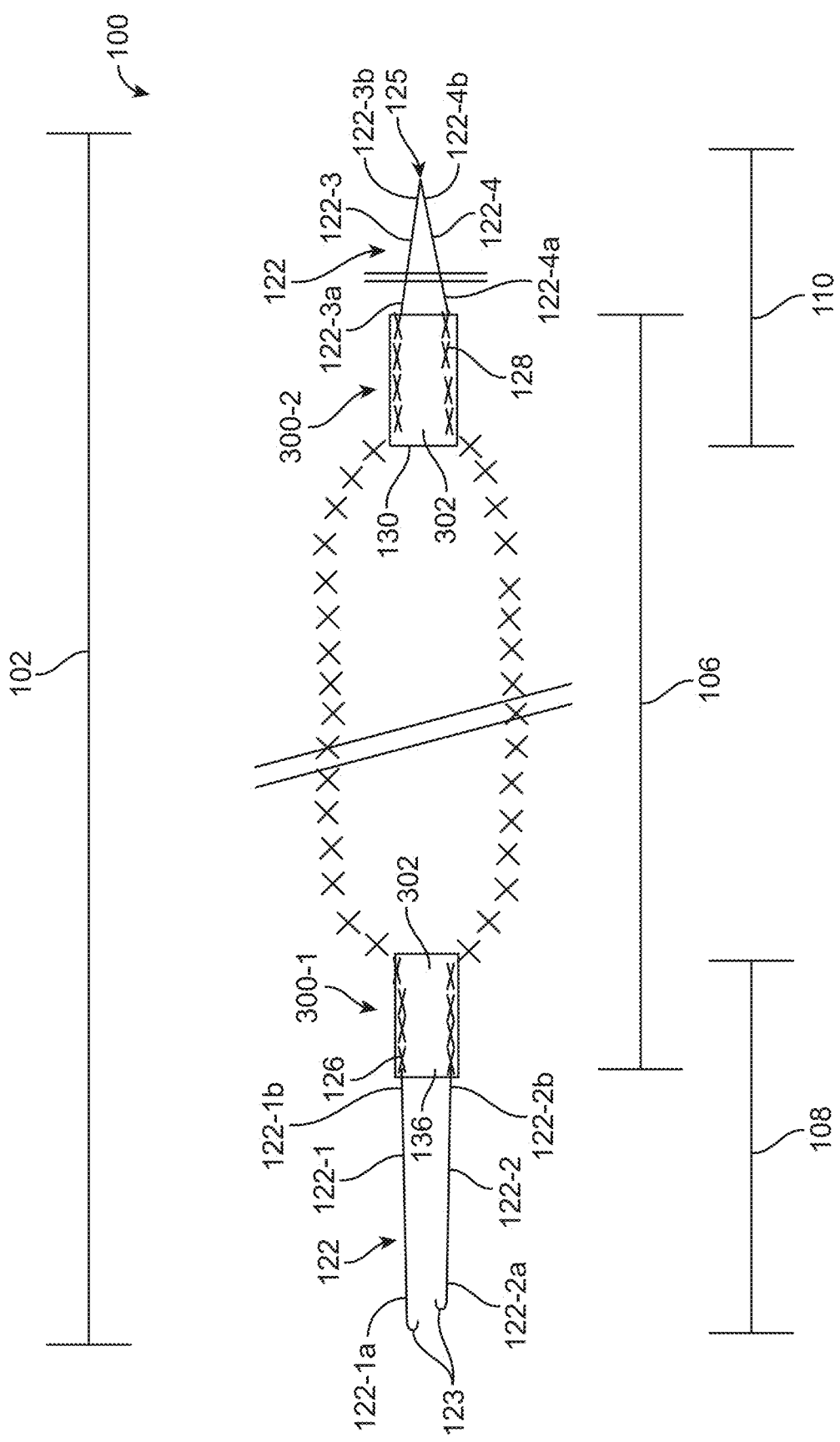
FIGS. 57-58 are longitudinal cross-section views of a further vaso-occlusive treatment system constructed according to disclosed embodiments.
Figure 58:
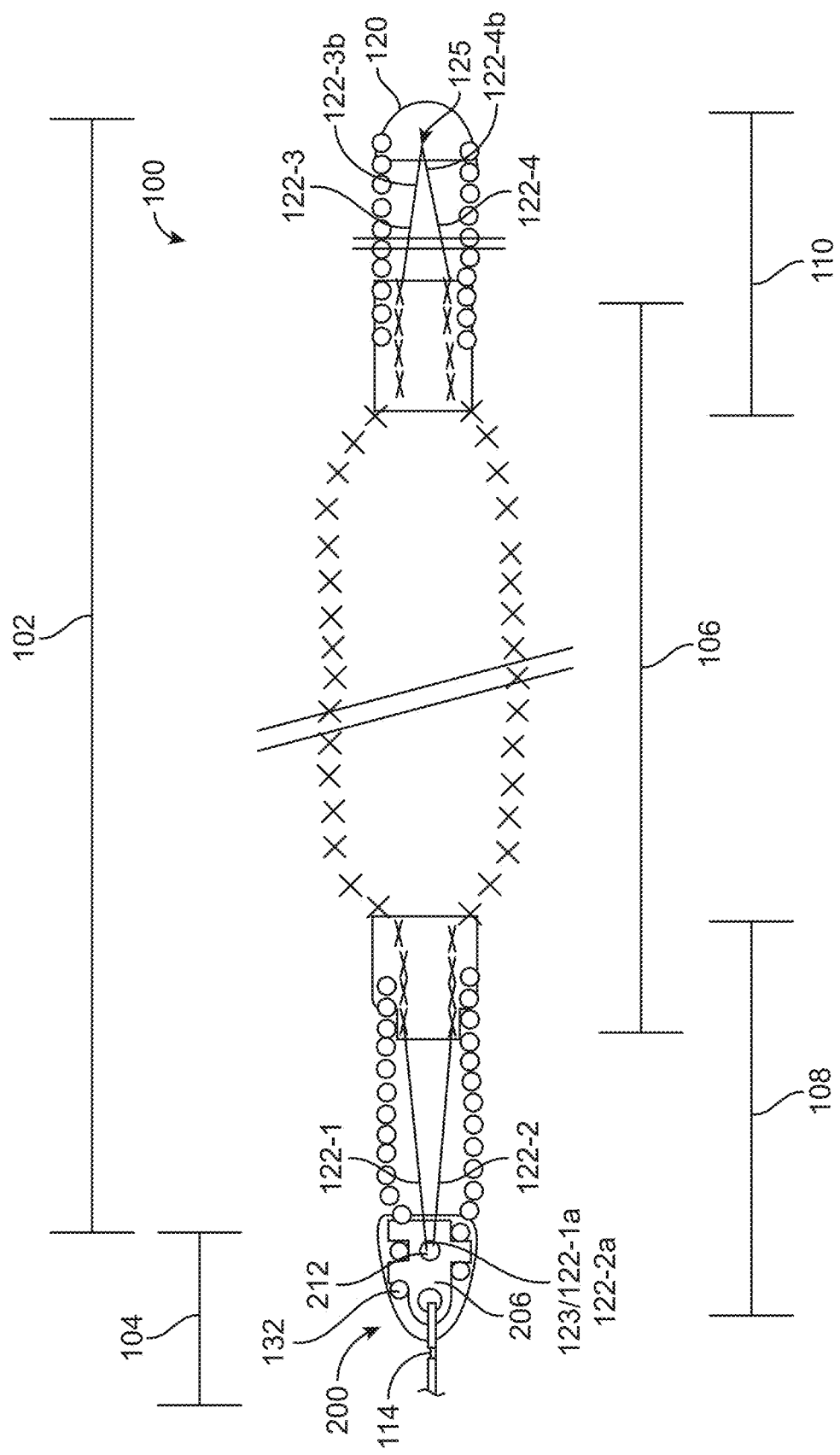

FIGS. 57 and 58 depict a vaso-occlusive treatment system 100 constructed according to yet another disclosed embodiment. The system 100 includes a vaso-occlusive device 102 having a central portion 106 configured to be coupled to proximal and distal portions 108, 110 (seen in FIG. 58) by respective proximal and distal intra-device junctions 300-1, 300-2. The central portion 106 is braided from DFT (i.e., composite) wires as described above, and has a substantially constant width (i.e., cross-sectional dimension). The proximal and distal intra-device junctions 300-1, 300-2 are mirror images of each other. The proximal intra-device junction 300-1 includes an open distal end 136 of the proximal portion 108 of the vaso-occlusive device 102 and a necked down proximal end 126 of the central portion 106 of the vaso-occlusive device 102. The proximal end 126 of the central portion 106 is necked down so that it fits inside of the open distal end 136 of the proximal portion 108. The proximal intra-device junction 300-1 also includes an adhesive drop 302, which permeates the coiled open distal end 136 of proximal portion 108 of the vaso-occlusive device 102. The adhesive 302 binds together the proximal end 126 of the central portion 106 of the vaso-occlusive device 102 and the open distal end 136 of the proximal portion 108 of the vaso-occlusive device 102, thereby forming the proximal intra-device junction 300-1. Further, the adhesive drop 302 also binds portions of the stretch-resisting member 122 extending into the proximal intra-device junction 300-1.

The stretch-resisting member 122 of the proximal portion 108 of the vaso-occlusive device 102 includes at least two members 122-1 and 122-2, each member formed from one or more wires extending from the proximal end 126 of the vaso-occlusive device 102. By way of non-limited example, the braided DFT wires at the proximal end 126 of the vaso-occlusive device 102 are trimmed to thereby form the stretch-resisting member 122 (i.e., members 122-1 and 122-2). The at least two members 122-1 and 122-2 have respective proximal ends 122-1a, 122-2a, and distal ends 122-1b, 122-2b. A hook 123 is formed at each of the proximal ends 122-1a and 122-2a of the respective stretch-resisting members 122-1 and 122-2. The hooks 123 are configured to be coupled to the link/adapter 206 of the major junction 200, shown in FIG. 58. The distal ends 122-1b and 122-2b of the respective stretch-resisting members 122-1 and 122-2 are coupled to the proximal intra-device junction 300-1.

The distal intra-device junction 300-2 includes a necked down distal end 128 of the central portion 106 of the vaso-occlusive device 102 and an open proximal end 130 of the distal portion 110 of the vaso-occlusive device 102. The distal end 128 of the central portion 106 is necked down so that it fits inside of the open proximal end 130 of the distal portion 110. The distal intra-device junction 300-2 also includes an adhesive drop 302, which permeates the coiled open proximal end 130 of the distal portion 110 of the vaso-occlusive device 102. The adhesive 302 binds together the distal end 128 of the central portion 106 of the vaso-occlusive device 102 and the open proximal end 130 of the distal portion 110 of the vaso-occlusive device 102, thereby forming the distal intra-device junction 300-2. Further, the adhesive drop 302 also binds the portion of the stretch-resisting member 122 extending into the distal intra-device junction 300-2.

The stretch-resisting member 122 of the distal portion 110 of the vaso-occlusive device 102 includes at least two members 122-3 and 122-4, each member formed from one or more wires extending from the distal end 128 of the braided vaso-occlusive device 102. For example, the braided DFT wires at the distal end 128 of the vaso-occlusive device 102 may be trimmed to thereby form the stretch-resisting member 122 (i.e., members 122-3 and 122-4). The two members 122-3 and 122-4 have respective proximal ends 122-3a, 122-4a, and distal ends 122-3b, 122-4b. Each of the proximal ends 122-3a and 122-4a of the respective stretch-resisting members 122-3 and 122-4 are coupled to the distal intra-device junction 300-2. The distal ends 122-3b and 122-4b of the respective stretch-resisting members 122-3 and 122-4 are jointly coupled forming a distal end joint 125. The joint 125 is formed by twisting the respective distal ends 122-3b and 122-4b together. The joint 125 may be formed by any other suitable coupling techniques, such as adhesive, bonding, welds, or the like. The joint 125 is configured to be coupled to the atraumatic distal tip 120, shown in FIG. 58.

As seen in FIG. 58, the vaso-occlusive treatment system 100 includes a vaso-occlusive device 102 coupled to a delivery assembly 104 by a major junction 200. The delivery assembly 104 includes an electrolytically degradable segment 114 at a distal end thereof. The central portion 106 of the vaso-occlusive device 102 is braided from DFT wires as described above. The proximal and distal portions 108, 110 are coils wound from one or more DFT wires as described above.

The vaso-occlusive treatment system 100 depicted in FIGS. 57-58 is similar to the system depicted in FIG. 9 and to the system partially depicted in FIG. 56. One difference with FIG. 9 is that system depicted in FIGS. 57-58 includes at least two sets of stretch-resisting members 122, each set is composed by one or more wires of the respective proximal end 126 and distal end 128 of the braided vaso-occlusive device 102. The first set of stretch-resisting members 122, including members 122-1 and 122-2, extend from the proximal end 126 of vaso-occlusive device 102 and the proximal intra-device junction 300-1 into the link/adapter 206 of the major junction 200. The second set of stretch-resisting members 122, including members 122-3 and 122-4, extend from the distal end 128 of the vaso-occlusive device 102 and intra-device junction 300-2 into the atraumatic distal tip 120. One difference with FIG. 56 is that the first set of stretch-resisting members depicted in FIGS. 57-58 includes two members 122-1 and 122-2, each having distal end hooks 123.

As shown in FIG. 58, the major junction 200 includes a link/adapter 206 coupled to both the distal end of the delivery assembly 104 and the open proximal end 132 of the proximal portion 108, thereby coupling the delivery assembly 104 and the proximal portion 108. The link 206 also includes a distal aperture 212. The hooks 123 at each of the proximal ends 122-1a and 122-2a of the respective stretch-resisting members 122-1 and 122-2 pass through the distal aperture 212 of the link 206, coupling the delivery assembly 104 and link 206 (and the proximal portion 108 coupled thereto).

The distal portion 110 of the system 100 of FIG. 58 has the atraumatic distal tip 120, which may be formed from a suitable amount of adhesive. The stretch-resisting members 122-3 and 122-4 extending from the distal intra-device junction 300-2 extend distally into the atraumatic distal tip 120. The distal ends 122-3b and 122-4b of the respective stretch-resisting members 122-3 and 122-4 are jointly coupled forming a distal end joint 125. The joint 125 is coupled to and/or disposed within the atraumatic distal tip 120.

Figure 59:
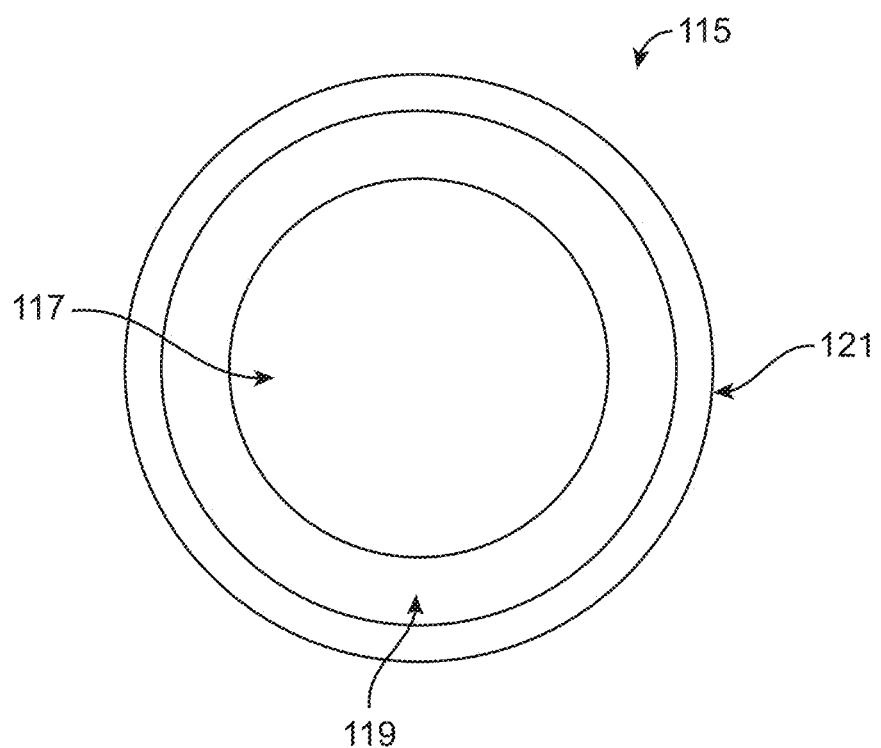
FIG. 59 is a cross-section view of an elongate member from which vaso-occlusive devices, or portions thereof, may be formed in accordance with the disclosed embodiments.

FIG. 59 depicts is a cross-section view of an elongate member from which the vaso-occlusive treatment system 100, the vaso-occlusive device 102, or portions thereof, may be formed. The elongate member 115 (e.g., "wire") comprises a core 117 composed of radiopaque materials, an intermediate layer 119 composed of superelastic materials, and an outer layer 121 composed of materials configured to provide oxidation protection. In the embodiment of FIG. 59, the wire 115 includes a substantially pure Platinum ("Pt") core 117 at least partially surrounded by a substantially pure Nitinol ("NiTi") intermediate layer 119; the intermediate layer 119 is at least partially surrounded by a substantially pure Titanium ("Ti") thin outer layer 121. As used in this application, the "thin" outer layer includes but is not limited to a range between about 0.001 to 20 micrometers. The Ti outer layer 121 is configured to avoid impacting or minimally impact on the flexibility and/or stiffness of the wire 115 and elements formed with wires 115 (e.g., braid). It should be appreciated that the thin outer layer 121 may be composed of other biocompatible materials with suitable density to provide an oxidation protection to the wire 115.

Variations on the thickness of the intermediate layer 119 and/or the outer layer 121, and/or variations on the diameter of the core 117, may be contemplated to optimize the desired features of the wire 115 (e.g., flexibility, stiffness, radio-opacity, or the like). The wire 115 may be manufactured by co-extrusion techniques or other suitable manufacturing techniques. For example, the Ti outer layer 121 can be applied on DFT wires as described above (Niti-DFT-40/5OPt) by plating, coating or Physical Vapor Deposition ("PVD").

Braids woven from wires 115 are suitable for vaso-occlusive applications. During heat set processing of braids formed with wires 115, the Ti outer layer 121 will oxidize to form Ni-free protection layer for the underlying intermediate NiTi layer 119. The use of wires 115 to form a braid is configured to eliminate the step of removing surface oxide by etching/EP and passivating processes, and/or eliminate Ni leaching issue in use. Further, the braid formed with wires 115 can be heat set in air environment.

As used herein, "stiffness" as it pertains to braids or portions thereof includes, but is not limited to, bending stiffness.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments, and are not intended as an exhaustive description of the disclosed inventions or as a limitation on the scope of the disclosed inventions, which is defined only by the appended claims and their equivalents. In addition, the respective illustrated embodiments need not each have all the aspects or advantages of features described herein. An aspect or an advantage described in conjunction with a particular embodiment of the disclosed inventions is not necessarily limited to that embodiment and can be practiced in any other embodiments even if not so illustrated.

The invention claimed is:

1. A vaso-occlusive treatment system, comprising:
a delivery assembly; and
a vaso-occlusive device detachably coupled to the delivery assembly by a delivery assembly junction, the vaso-occlusive device comprising
a braided portion formed out of one or more composite wires, each composite wire comprising a core made from a core metallic material, and an external layer made from an external metallic material different from the core metallic material, wherein one of the core and the external layer has a greater radiopacity and a greater stiffness, respectively, than the other one of the core and the external layer,
a coiled portion, and
an intra-device junction coupling the braided portion to the coiled portion,
wherein the delivery assembly junction comprises a braided member,
wherein at least a portion of the braided member is disposed inside of the vaso-occlusive device, and
wherein the delivery assembly junction further comprises an adhesive that binds together a proximal end of the vaso-occlusive device and the braided member.

2. The vaso-occlusive treatment system of claim 1, wherein the core metallic material comprises platinum, and the external metallic material comprises Nitinol.

3. The vaso-occlusive treatment system of claim 1, wherein the core metallic material comprises Nitinol, and the external metallic material comprises platinum.

4. The vaso-occlusive treatment system of claim 1, wherein each of the one or more composite wires has a yield strength to ultimate strength ratio of less than 70%.

5. The vaso-occlusive treatment system of claim 1, each composite wire having a core comprising platinum and an external layer comprising Nitinol,
wherein the plurality of composite wires consists of 16-48 composite wires,
wherein each composite wire has a platinum content of 35% to 60% by volume, and
wherein each composite wire has an outer diameter of 0.0010 in to 0.0015 in.

6. The vaso-occlusive treatment system of claim 5, wherein the plurality of composite wires consists of 24-32 composite wires, each having a platinum content of 40% to 50% by volume, and an outer diameter of 0.00115 in. to 0.00125 in.

7. The vaso-occlusive treatment system of claim 1, the delivery assembly having a distal end, wherein the distal end forms a hook.

8. The vaso-occlusive treatment system of claim 1, the intra-device junction comprising a tubular body disposed around least a portion of the vaso-occlusive device.

9. The vaso-occlusive treatment system of claim 1, the intra-device junction comprising a pin extending radially through the braided and coiled portions, thereby coupling the braided and coiled portions.

10. The vaso-occlusive treatment system of claim 1, wherein the braided portion has a substantially constant width.

* * * * *